US006136585A

United States Patent [19]

Ball et al.

[11] Patent Number: 6,136,585

[45] Date of Patent: Oct. 24, 2000

[54] ATTENUATION OF NEGATIVE STRANDED RNA VIRUSES BY REARRANGEMENT OF GENES AND USES THEREOF

[75] Inventors: L. Andrew Ball; Gail W. Wertz, both of Birmingham, Ala.

[73] Assignee: UAB Research Foundation, Birmingham, Ala.

[21] Appl. No.: 09/071,606

[22] Filed: May 1, 1998

Related U.S. Application Data

[60] Provisional application No. 60/045,471, May 2, 1997.

[51] Int. Cl.[7] ............................ C12N 7/04; A61K 39/205

[52] U.S. Cl. ......................................... 435/236; 424/224.1

[58] Field of Search .......................... 435/236; 424/224.1

[56] References Cited

PUBLICATIONS

Wertz et al., Gene rearrangement attenuates expression and lethality of a nonsegmented negative strand RNA virus. Proc. Natl. Acad. Sci. USA 95(7):3501–3506, 1998.

*Primary Examiner*—Donna C. Wortman
*Attorney, Agent, or Firm*—Benjamin Aaron Adler

[57] ABSTRACT

Provided is a method of attenuating a virus of the order Mononegavirales, comprising the step of: rearranging said virus' gene order by moving a gene essential for RNA replication away from its wild-type 3' promoter proximal position site, wherein said gene is an essential limiting factor for genome replication and is placed in the next to last position in the gene order. Also provided is a method of making an attenuated virus useful for a vaccine, comprising the steps of: rearranging said virus' gene order by moving a gene essential for RNA replication away from its wild-type 3' promoter proximal position site, wherein a gene which is a n essential limiting factor for genome replication is placed in the next to last position in the gene order; and placing a gene coding for an immune response inducing antigen in the position closest to the 3' end of the gene order. Also provided is a method of attenuating a virus of the order Mononegavirales, comprising the step of: rearranging said virus' gene order.

11 Claims, 19 Drawing Sheets

| | |
|---|---|
| R4 (Wild-type) | 3'- leader - N - P - M - G - L - trailer - 5' |
| R1 | 3'- leader - N - G - M - P - L - trailer - 5' |
| R2 | 3'- leader - N - M - G - P - L - trailer - 5' |
| R3 | 3'- leader - N - P - G - M - L - trailer - 5' |
| R5 | 3'- leader - N - G - P - M - L - trailer - 5' |
| R6 | 3'- leader - N - M - P - G - L - trailer - 5' |
| R7 | 3'- leader - P - N - M - G - L - trailer - 5' |
| R8 | 3'- leader - P - M - N - G - L - trailer - 5' |
| R9 | 3'- leader - P - M - G - N - L - trailer - 5' |
| R10 | 3'- leader - G - N - P - M - L - trailer - 5' |
| R11 | 3'- leader - G - P - M - N - L - trailer - 5' |

FIG. 1

BspM1 5′ ...ACCTGCNNNN 3′
3′ TGGACGNNNNNNNN 5′ (SEQ ID No. 4)

Bsa1 5′...GGTCTCN 3′
3′ .CCAGAGNNNNN 5′ (SEQ ID No. 5)

Upstream PCR primer (Hind3, BspM1) 5′ GGGAAGCTTACCTGCACTAACAGNNATNNN 3′ (SEQ ID No. 6)

VSV IC junction 5′...TATGAAAAAACTAACAGNNATNNN...3′ (SEQ ID No. 7)
3′...ATACTTTTTTGATTGTCNNTANNN...5′

Downstream PCR primer 3′ CTTTTTTTGATTGTCNNTACGTCCAGGGCCCACG 5′ (BspM1, Ava1) (SEQ ID No. 8)

GCACCCGGGACCTGCATATCTGTTACTTTTTTTC P Downstream (SEQ ID No. 9)
GCACCCGGGACCTGCATCTCTGTTAGTTTTTTTC M Downstream (SEQ ID No. 10)
GCACCCGGGACCTGCATTGCTGTTAGTTTTTTTC G Downstream (SEQ ID No. 11)

GCACCCGGGACCTGCATATCTGTTACTTTTTTTC Consensus downstream (SEQ ID No. 12)
CG
T

FIG. 3A

| | *Acc1* | *Bgl2* | *Pst1* |
|---|---|---|---|
| NGMPL | 0.43+3.67 | 1.84+2.26 | 1.16+2.94 kb |
| NMGPL | As R1 | 0.61+3.49 | 2.00+2.10 |
| NPGML | 1.16+2.94 | 0.99+3.11 | 1.98+2.12 |
| NPMGL | As R3 | 1.42+2.68 | 1.29+2.81 |
| NGPML | 1.26+2.84 | As R3 | As R1 |
| NMPGL | 2.07+2.03 | As R2 | As R4 |

| % of WT | | | | |
|---|---|---|---|---|
| Genome | 100 | 49 | 26 | 4 |
| N mRNA | 100 | 36 | 6 | 3 |

ATTENUATION OF NEGATIVE STRANDED RNA VIRUSES BY REARRANGEMENT OF GENES AND USES THEREOF

CROSS REFERENCE TO RELATED APPLICATION

This application claims benefit of priority of Provisional Application U.S. Ser. No. 60/045,471 filed May 2, 1997.

BACKGROUND OF THE INVENTION

1. Field of the Invention

The present invention relates generally to the fields of molecular virology and vaccinology. More specifically, the present invention relates to the attenuation of negative stranded RNA viruses by rearrangement of their genes and uses thereof.

2. Description of the Related Art

Live attenuated viruses capable of replicating to generate protective humoral as well as cell mediated immune responses without producing disease manifestations have proven effective vaccines against viruses such as smallpox, yellow fever and poliomyelitis. The strategy for attenuation, however, has been empirical in most cases and not reproducible for general use. An additional consideration in the case of RNA viruses is that the high error rate of RNA dependent RNA polymerases, their lack of proof reading and the quasi-species nature of RNA virus populations (Domingo et al, 1996), make the use of live attenuated viruses for this large group of medically significant pathogens problematic. This is especially true if the vaccine virus is based on a limited number of single base changes as mutation to virulence is a potential problem. For example, only a few back mutations can restore virulence to the Sabin poliovirus type 3 vaccine strain (Wimmer et al., 1993).

The non-segmented negative strand RNA viruses of the family Mononegavirales possess an elegantly simple means of controlling the expression of their genes. The linear, single-stranded RNA genomes of this family encode five to ten genes, the order of which is highly conserved among all members. The prototype virus of this family is the Rhabdovirus, vesicular stomatitis virus (VSV). Transcription of the viral genome is carried out by the virus encoded RNA dependent RNA polymerase. There is a single entry site on the linear genome for the RNA polymerase, yet the mRNAs of the virus are not produced in equimolar amounts.

Available evidence indicates that the linear order of the genes on the genome controls the levels of expression of individual genes. Transcription initiates at the single polymerase entry site at the 3' terminus of the genome and is obligatorily processive (Ball and White, 1976). The level of expression of the individual genes as monocistronic mRNAs is controlled by the dissociation, approximately 30% of the time, of the polymerase at each intergenic junction, as it traverses the genome in the 3' to 5' direction (Iverson and Rose). This mechanism of transcription results in sequentially decreasing amounts of the transcripts of each gene as a function of the distance of the gene from the 3' terminus of the genome. Correspondingly, gene products needed in stoichiometric amounts to support replication, such as the nucleocapsid (N) protein, are encoded at or near the 3' terminus in all cases and expressed in the highest molar amounts (Villarreal e t al., Ball and White). Gene products needed in enzymatic amounts, such as the RNA polymerase are encoded most distal from the 3' end. In all cases, the polymerase gene is the 5'-most gene, expressed in the lowest amount. Precise molar ratios of the proteins are required for optimal replication. For successful replication, proteins must be expressed in molar ratios that approximate those expressed normally from the genome (Pattnaik and Wertz, 1990).

Viruses of the family Mononegavirales do not undergo homologous genetic recombination (Pringle, 1987). Thus, other than defective interfering particles, which lack portions of the genome, variants of these viruses having the entire complement of genes in a rearranged format have not been observed in nature.

The prior art is deficient in the lack of effective means of attenuating negative stranded RNA viruses by rearrangement of their genes and uses of such attenuated viruses for vaccines. The present invention fulfills this longstanding need and desire in the art.

SUMMARY OF THE INVENTION

The non-segmented negative-strand RNA viruses (order Mononegavirales) comprise several important human pathogens. The order of their genes, which is highly conserved, is the major determinant of the relative levels of gene expression, since genes that are close to the single promoter site on the viral genome are transcribed at higher levels than those that occupy more distal positions. An infectious cDNA clone of the prototypic vesicular stomatitis virus (VSV) was manipulated to rearrange the order of four of the five viral genes, while leaving all other aspects of the viral nucleotide sequence unaltered. In one set of cDNA clones, the middle three genes (which encode the phosphoprotein P, the matrix protein M, and the glycoprotein (C) were rearranged into all six possible orders. In another set, the gene for the nucleocapsid protein N was moved away from its wild-type promoter-proximal position and placed second, third or fourth. In a final rearrangement, the G protein gene, which encodes the major surface antigen and the target for neutralizing antibodies, was put next to the promoter, in the position for maximum expression. Infectious viruses were recovered from each of these rearranged cDNAs and examined for their levels of gene expression, growth potential in cell culture, and virulence in mice. Rearrangement changed the expression levels of the encoded proteins and attenuated the viruses to different extents both in cultured cells and in mice. Since the Mononegavirales do not undergo homologous recombination, gene rearrangement should be irreversible and thus provides a rational method for developing securely attenuated live vaccines against this type of virus.

In one embodiment of the present invention, there is provided a method of attenuating a virus of the order Mononegavirales, comprising the step of: rearranging said virus' gene order by moving a gene away from its wild-type 3' promoter proximal position site, wherein said gene is an essential limiting factor for genome replication and wherein said gene is placed in the next to last position in the gene order.

In another embodiment of the present invention, there is provided a method of making an attenuated virus useful for a vaccine, comprising the steps of: rearranging said virus' gene order by moving a gene away from its wild-type 3' promoter proximal position site, wherein a gene which is an essential limiting factor for genome replication is placed in the next to last position in the gene order; and placing a gene coding for an immune response inducing antigen in the position closest to the 3' end of the gene order.

In yet another embodiment of the present invention, there is provided a method of attenuating a virus of the order Mononegavirales, comprising the step of: rearranging said virus' gene order by moving a gene away from its wild-type position.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the gene orders of the rearranged VSV genomes.

FIG. 3A shows the cleavage specificity of restriction enzymes used to generate cDNA modules for gene order rearrangement. Using PCR, either the BspMI or BsaI is positioned at each end of the P, M and G genes of VSV, and at the 3' end of the N gene and the 5' end of the L gene, such that the sticky ends correspond to 4 of the conserved nucleotides at the intercistronic junctions.

Cytoplasmic extracts were prepared and RNA was extracted and analyzed on 1.75% agarose urea gels as described below. The letters L, G, N, M and P indicate the positions of the respective VSV mRNAs.

Figure 7:
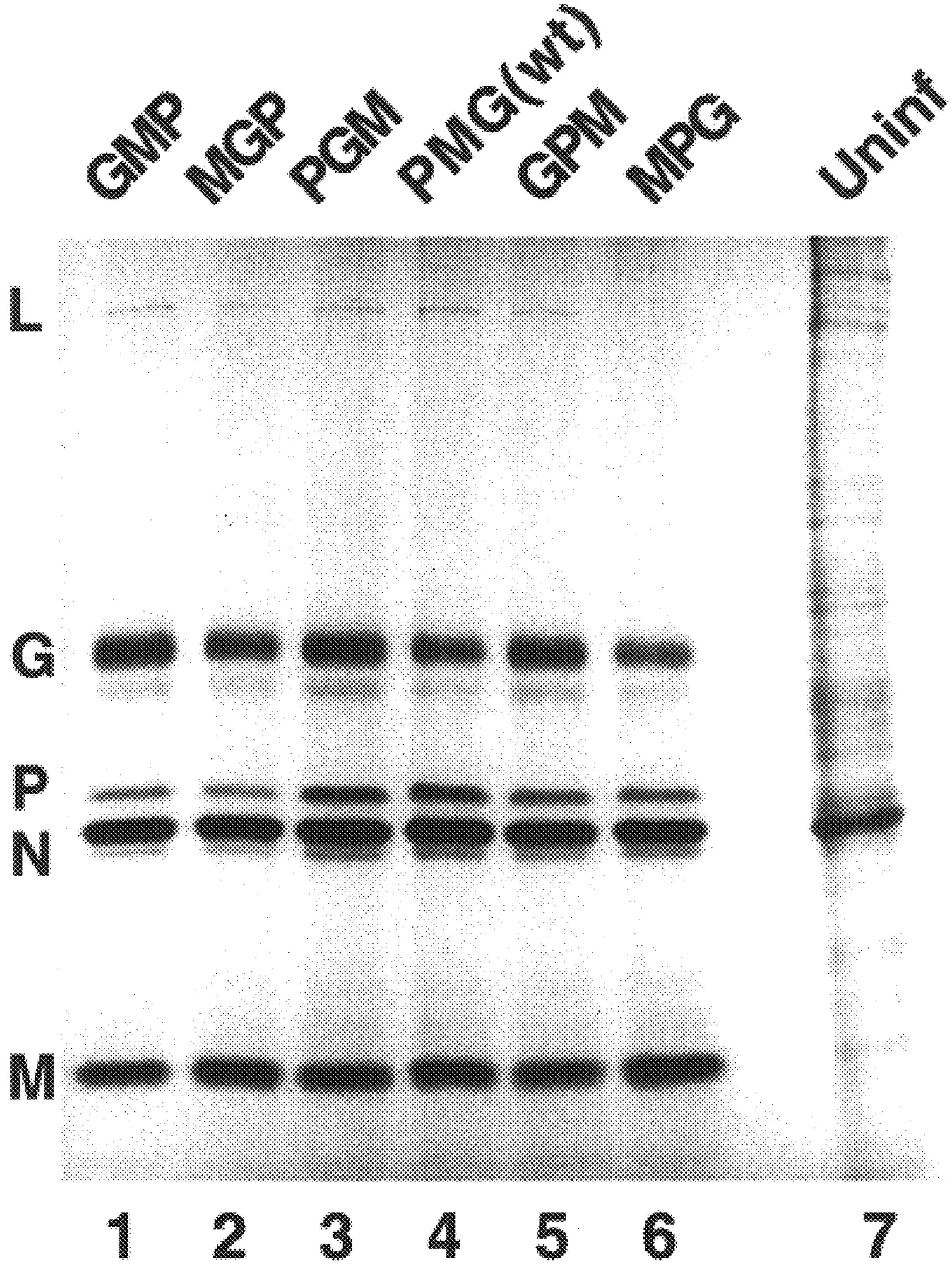

FIG. 7 shows the viral specific proteins synthesized in BHK-21 cells infected with rearranged viruses GMP, MGP, PGM, PMG (wt), GPM and MPG. Cells were infected with virus at a multiplicity of 3 and proteins were labeled with [$^{35}$S]-methionine for 30 minutes at 4 hours postinfection. Cytoplasmic extracts were prepared and proteins were analyzed on 10% polyacrylamide gels. The letters L, G, P, N, and M indicate the positions of the respective VSV proteins.

FIG. 8 shows the molar ratios of proteins synthesized in BHK-21 cells infected with rearranged viruses as determined by densitometric scanning of autoradiographs of gels such as shown in FIG. 7. Graphs in Panel A show a n arrangement (x-axis) according to the wild-type gene order, or in Panel B, according to the order in each rearranged virus.

Figure 9:
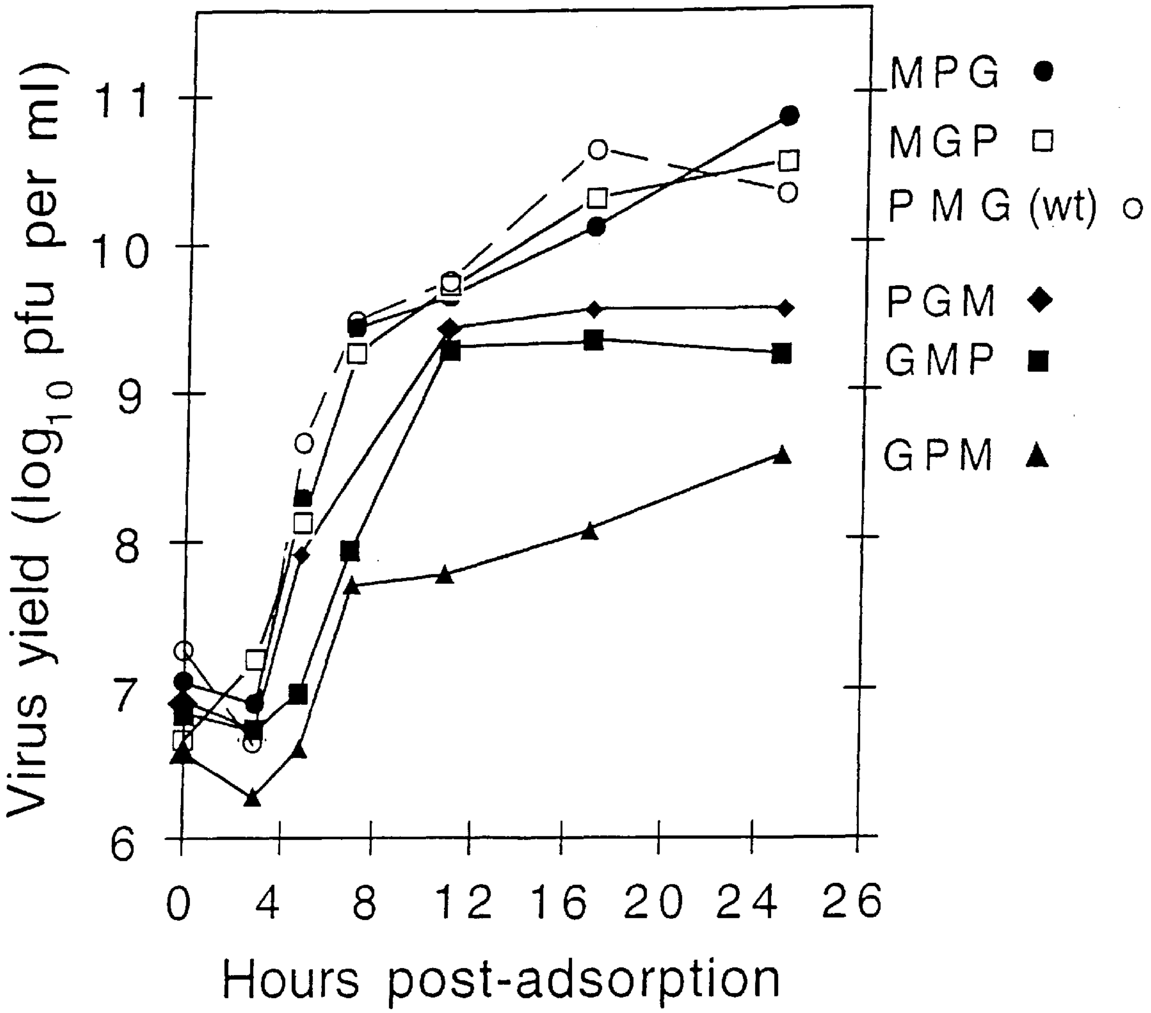

FIG. 9 shows the single step growth curve for replication of rearranged viruses in BSC-1 cells. Input multiplicity of infection was 1 and viral production was measured over a 25 hour period and analyzed by plaque assay.

Figure 10:
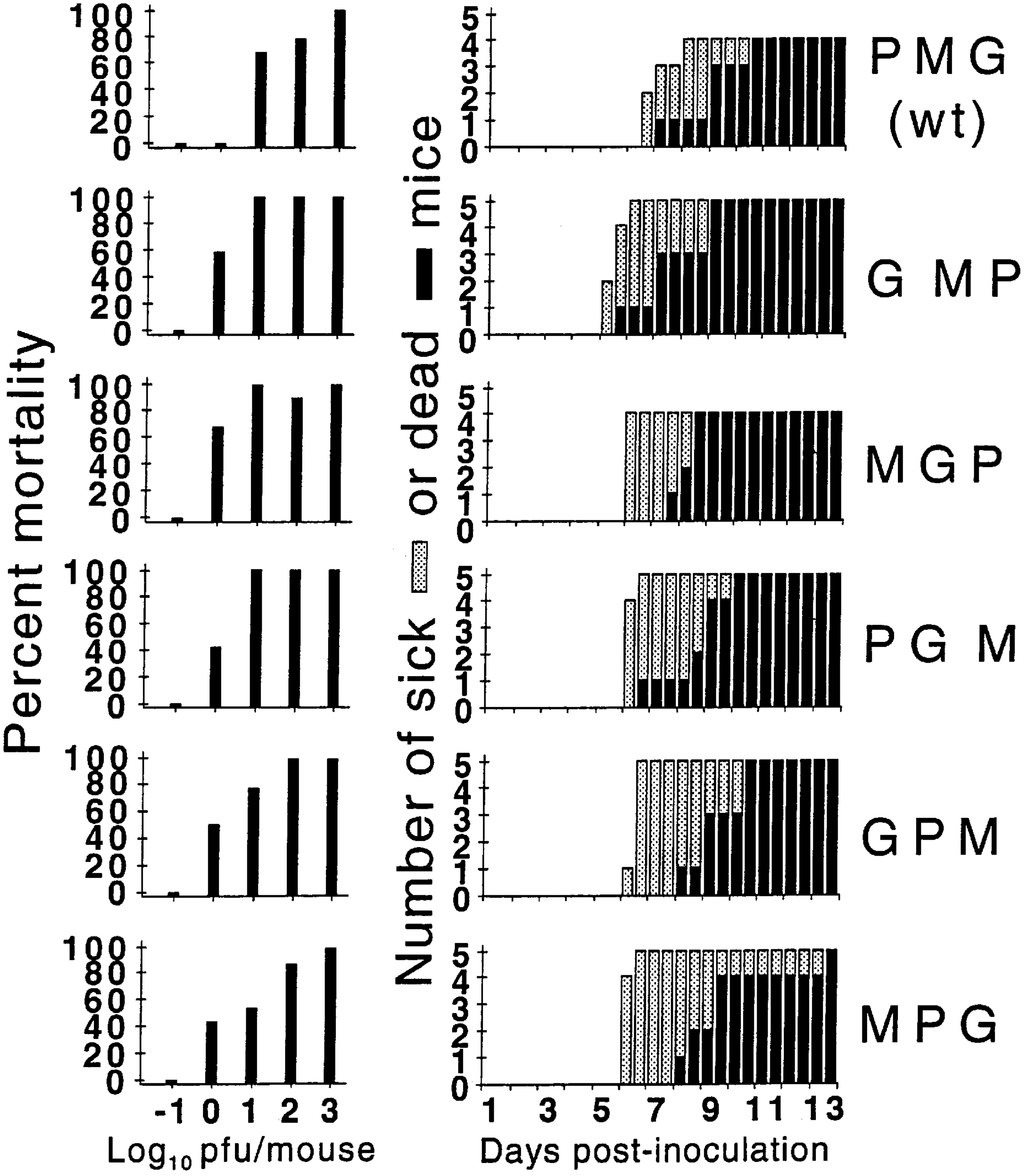

FIG. 10 shows lethality of rearranged viruses for mice and days to sickness and death following intranasal inoculation of serial ten-fold doses.

Figure 11:
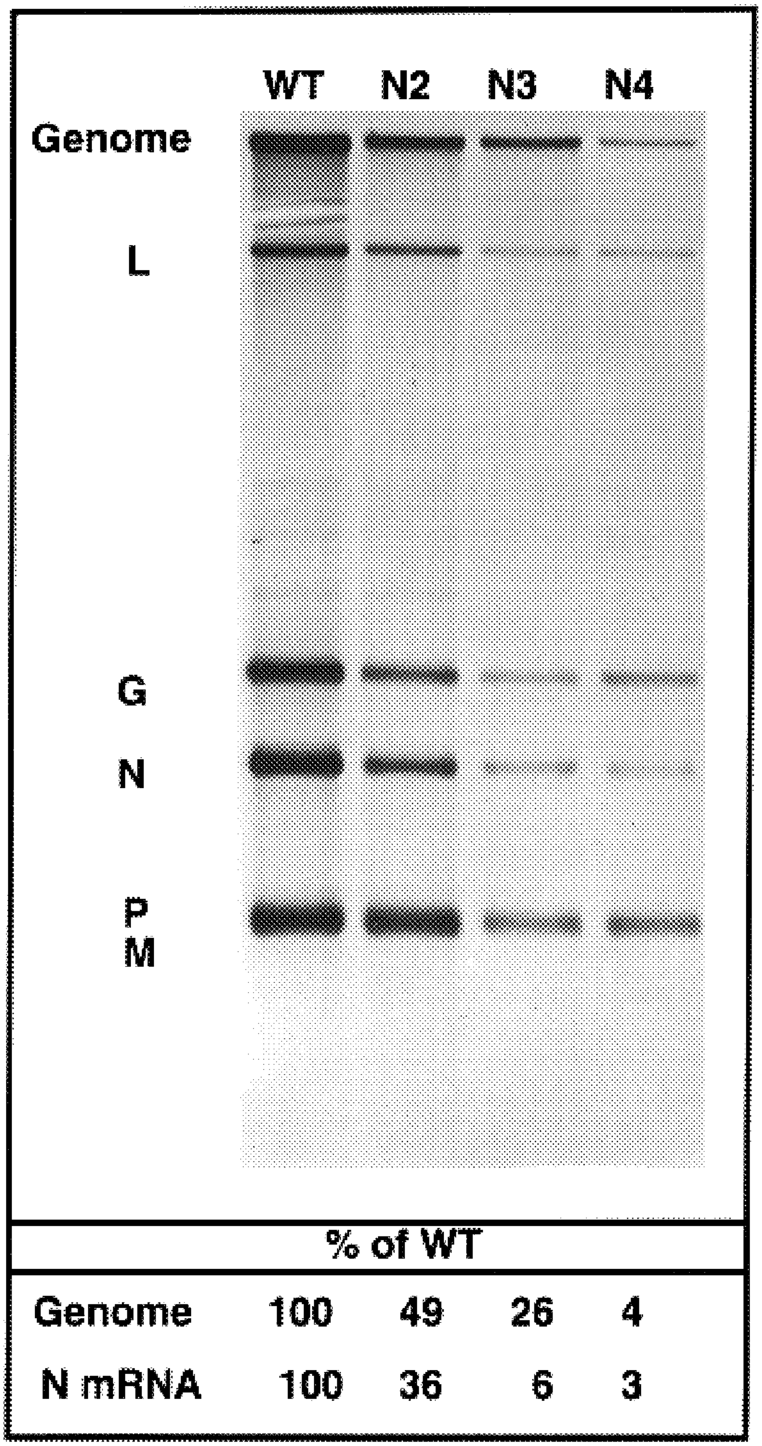

FIG. 11 shows the viral specific RNA synthesized in BHK-21 cells infected with rearranged viruses N1 (wt), N2, N3 and N4. Conditions of infection, labeling and analysis were as described in FIG. 6.

Figure 12:
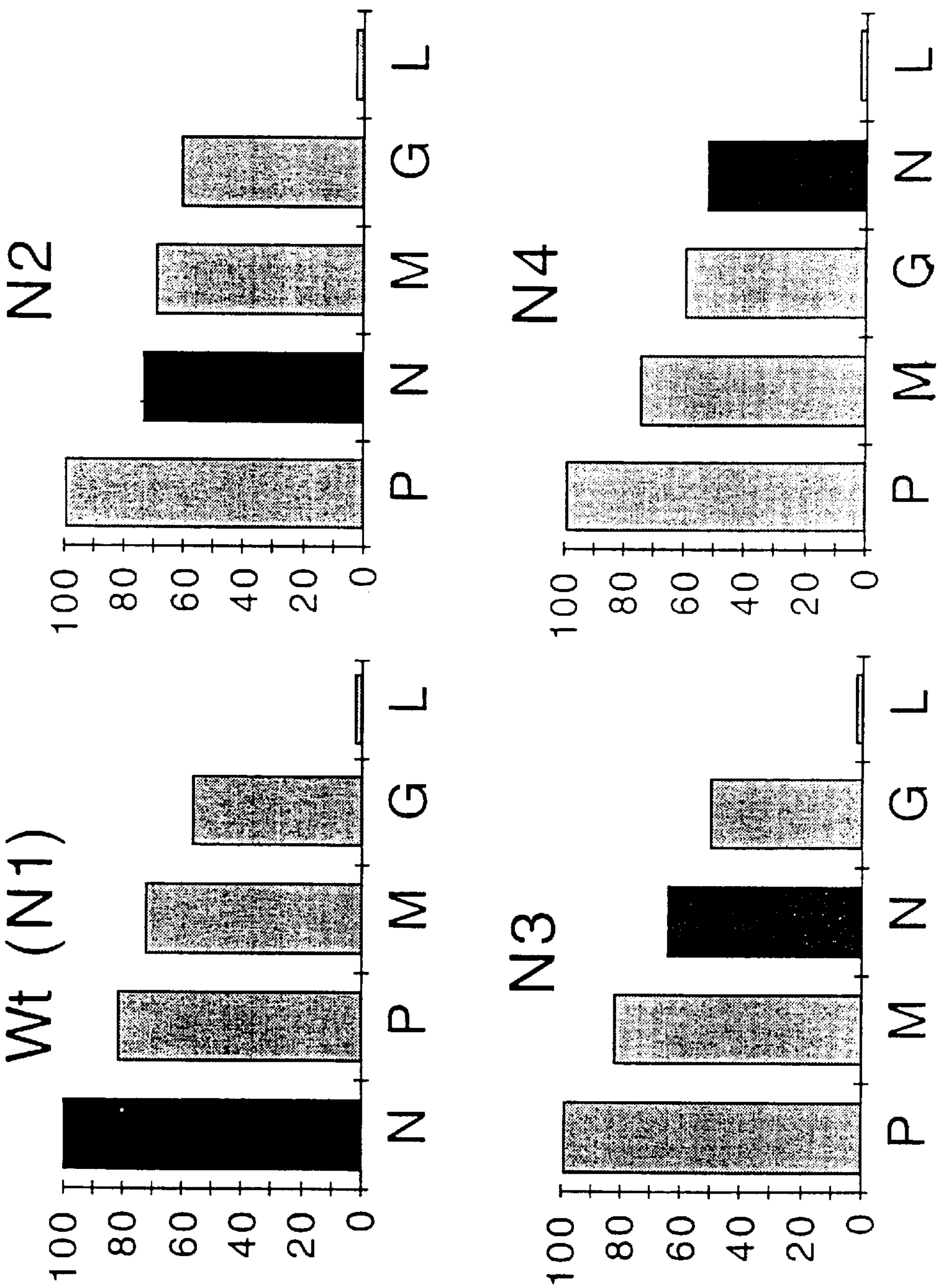

FIG. 12 shows the molar ratios of the VSV specific proteins synthesized in BHK-21 cells following infection with rearranged viruses N1 (wt), N2, N3 and N4. Proteins were analyzed as described in FIG. 7 and molar ratios calculated as described in FIG. 8.

Figure 13:
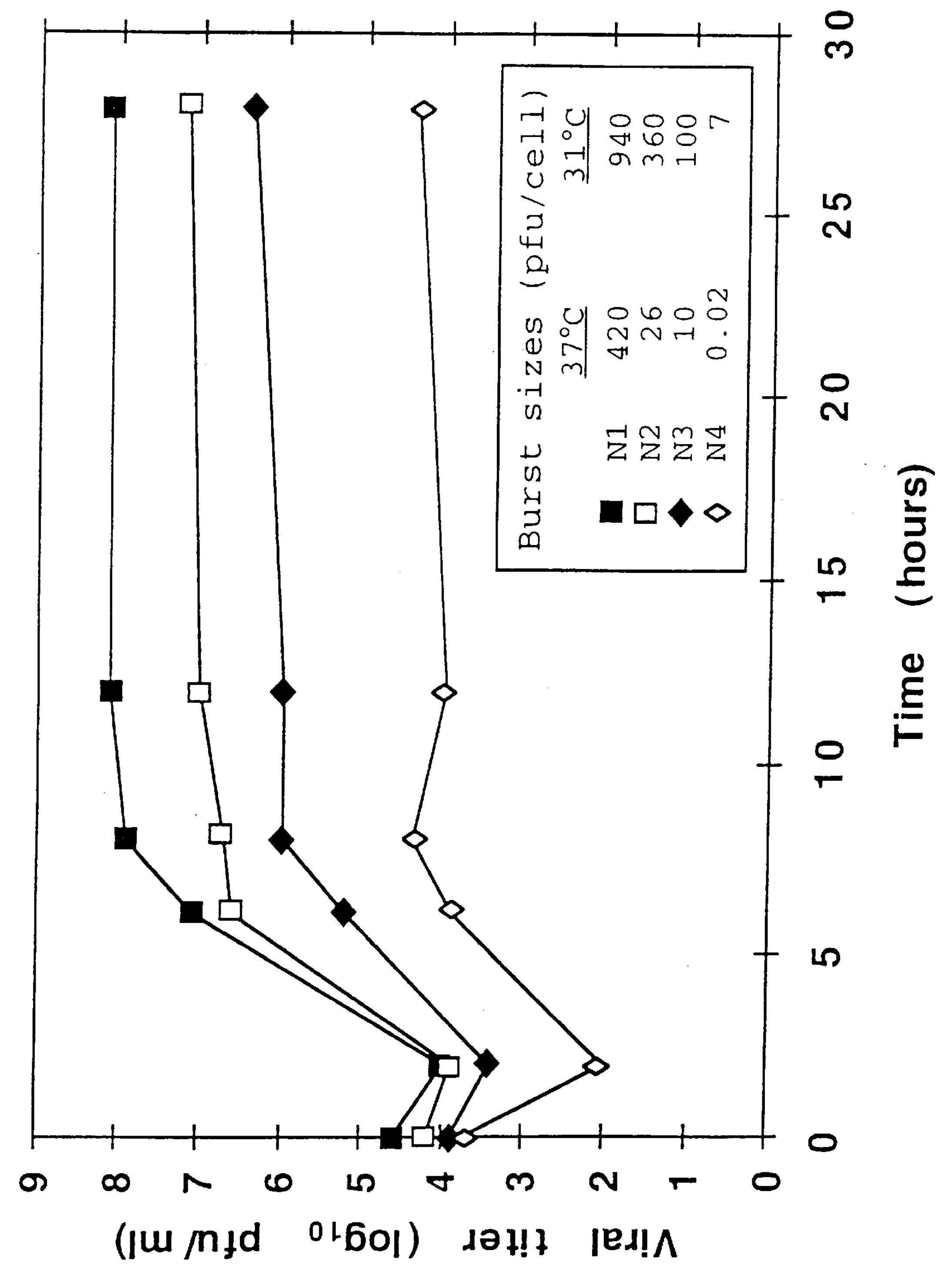

FIG. 13 shows replication of viruses with N gene translocations by single step growth in BHK cells.

Figure 14:
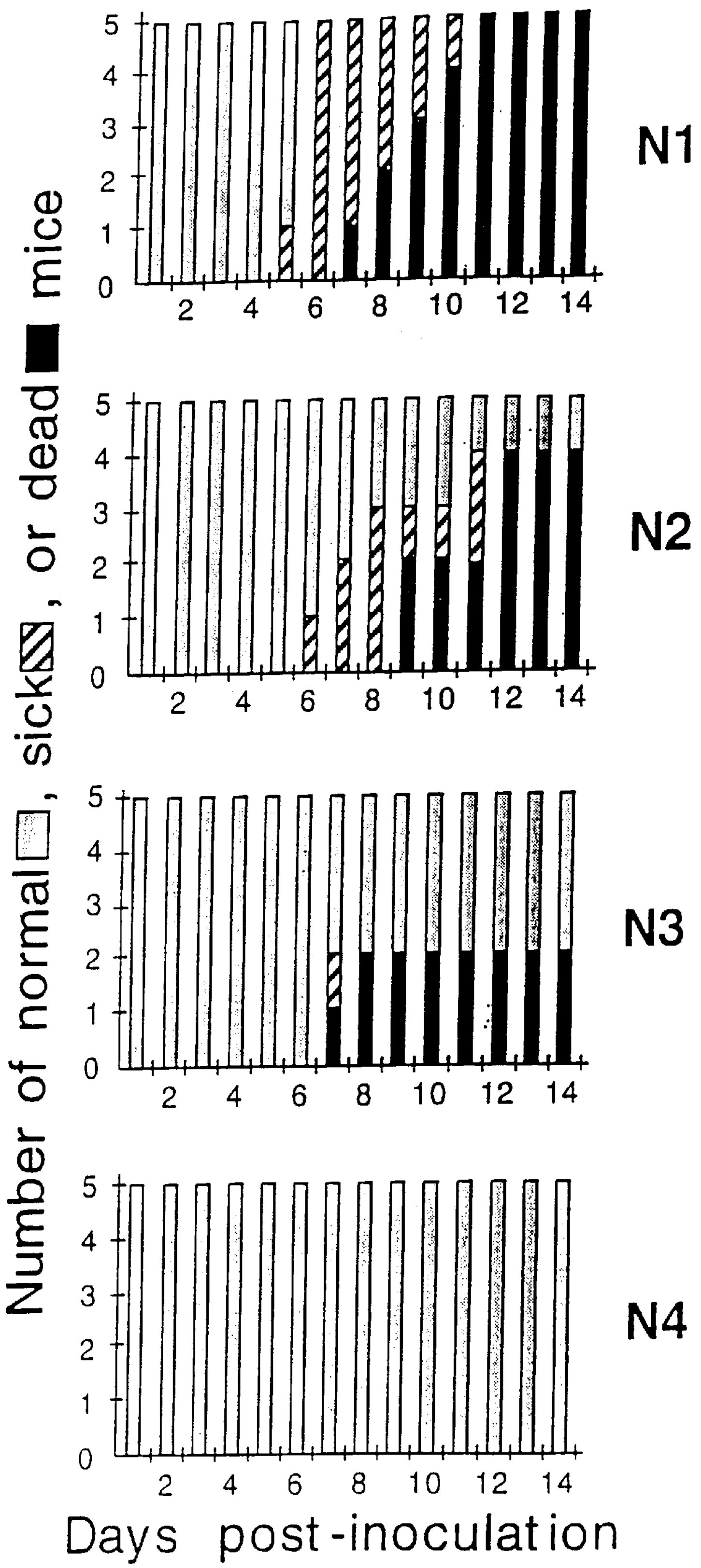

FIG. 14 shows relative lethality of viruses N1 (wt), N2, N3 and N4 for mice.

Figure 15:
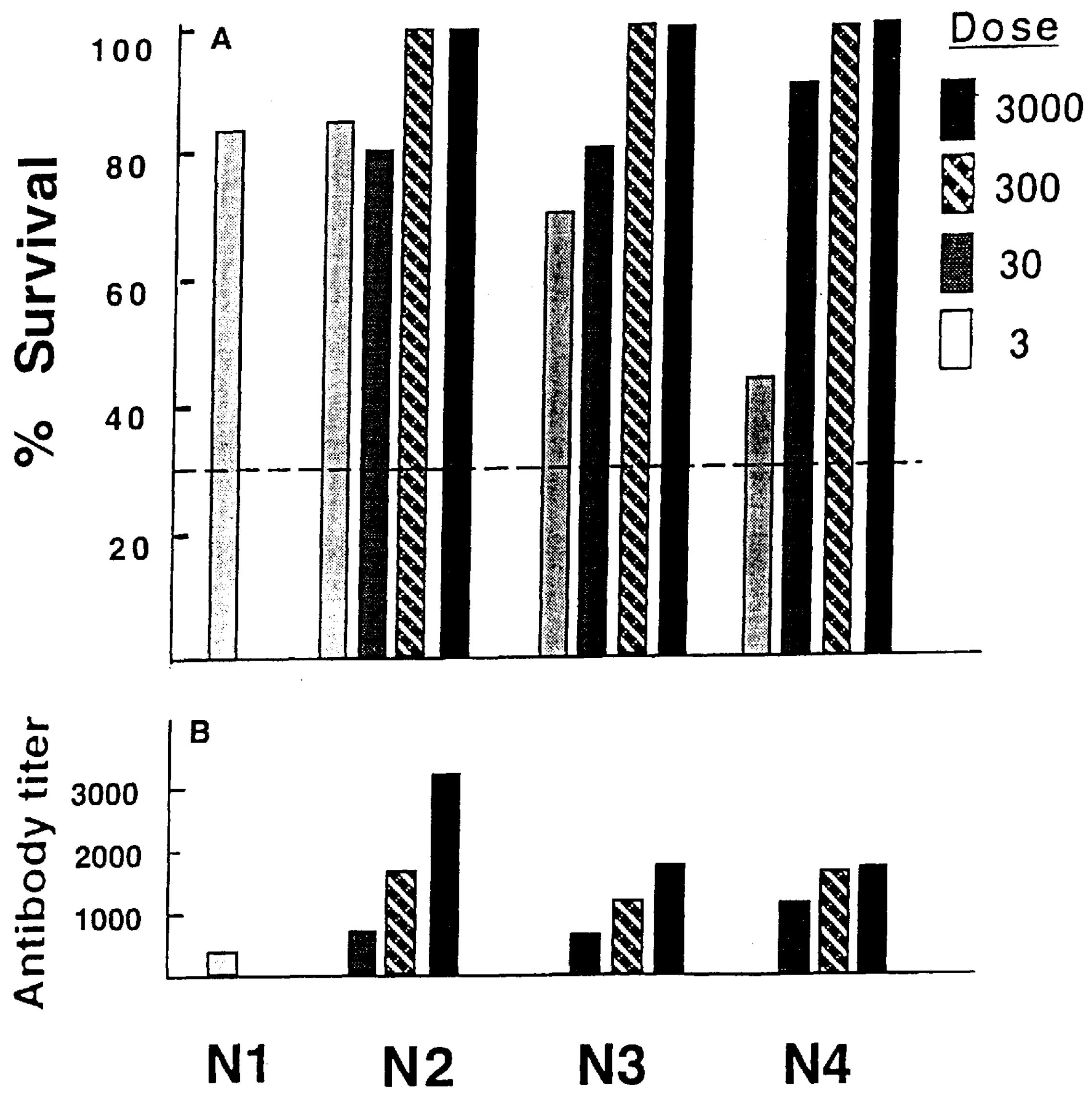

FIG. 15 shows a comparison of antibody production and ability to protect against lethal challenge for viruses N1 (wt), N2, N3 and N4.

Figure 16:
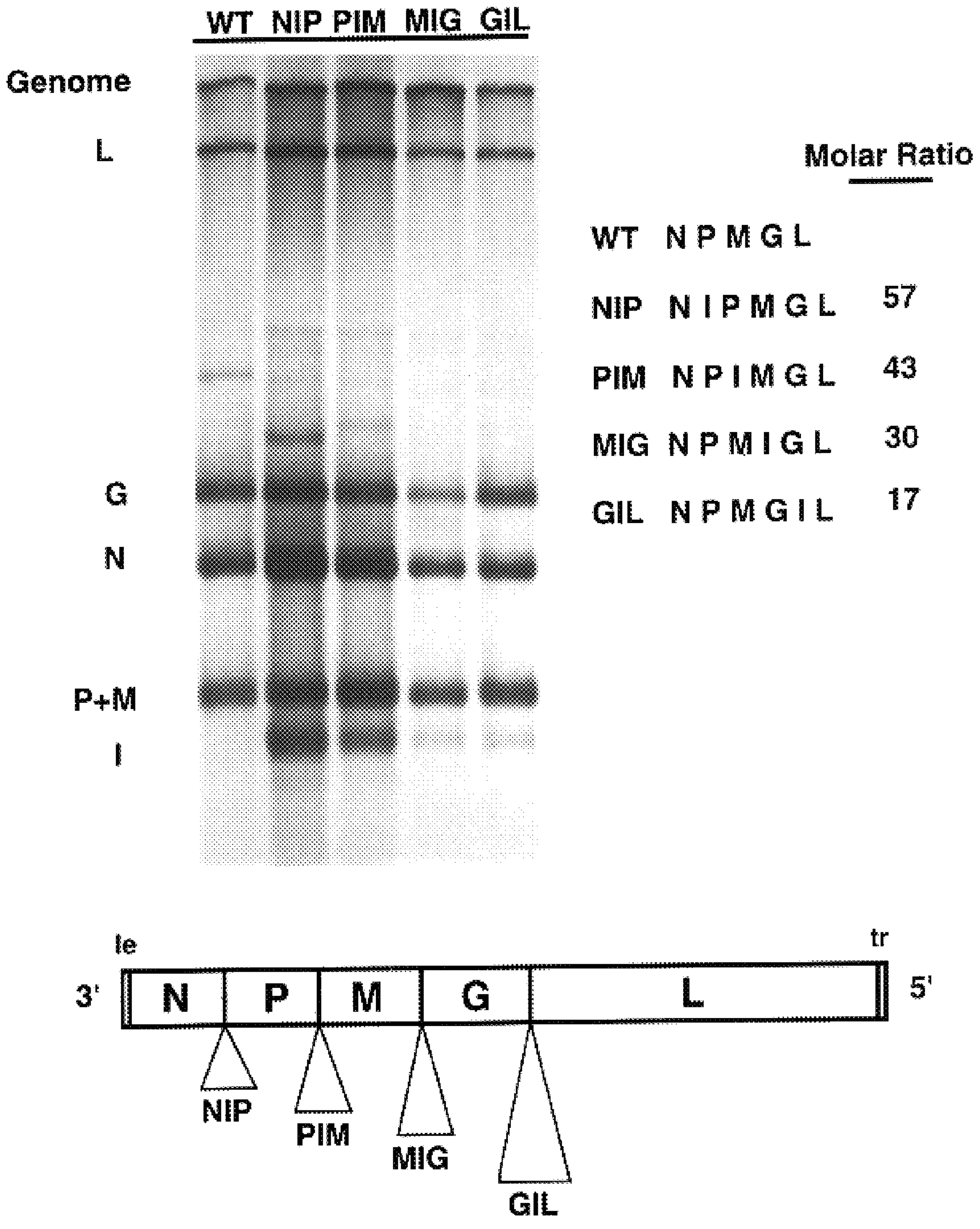

FIG. 16 shows the viral specific RNA synthesized in BHK-21 cells infected with viruses containing a foreign gene (I) inserted at each VSV intergenic junction. Conditions of infection, labeling and analysis are as described in FIG. 6 except the labeling time was from 2 to 4.5 hours postinfection.

DETAILED DESCRIPTION OF THE INVENTION

The ability to introduce specific changes into the genome of a negative strand RNA virus allowed translocation of the gene for the N protein to successive positions on the genome and demonstrated directly that the position of a gene relative to the promoter determined the level of expression. Levels of N protein synthesis control the level of RNA replication. Consistent with this, the present invention demonstrates that as the level of N mRNA synthesis and protein synthesis in cells infected with viruses N2, N3 and N4 was reduced, the level of genomic RNA replication also was reduced. Correspondingly, the production of infectious virus in cell culture was reduced in increments up to four orders of magnitude with virus N4. Finally, concomitant with reduced replication potential, the lethality of viruses N2, N3, and N4 for mice following IN inoculation was reduced by approximately one, two or three orders of magnitude, respectively, compared to the wild-type virus.

These data demonstrate that translocating a single gene essential for replication to successive positions down the viral genome lowered the growth potential in cell culture and the lethality of the viruses for mice in a stepwise manner. However, the ability of the viruses to elicit a protective immune response in mice was not altered in correspondence with the reduction in virulence. Therefore, since the viruses all contained the wild-type complement of genes and all were competent to replicate, albeit at reduced levels, the level of replication was sufficient to induce a protective host response. Thus, for some rearranged viruses, the protective dose and the lethal dose were 1,000 fold different, in contrast to the situation with wild-type virus where the lethal dose and protective dose overlap. Taken together, these data suggest a means of attenuating non-segmented negative strand RNA viruses in a predictable, incremental manner that would allow one to determine an optimal level of attenuation to avoid disease production without loss of replication potential to induce a sufficient immune response.

Since the Mononegavirales have not been observed to undergo homologous recombination, gene rearrangement is predicted to be irreversible, and therefore, the present invention provides a rational, alternative method for developing stably attenuated live vaccines against the non-segmented negative strand RNA viruses. Furthermore, based on the close similarity of genome organization and control of gene expression, this approach to generating attenuated viruses should be applicable to the entire family of Mononegavirales, which includes the Rhabdoviridae, such as rabies, the Paramyxoviridae, such as measles, mumps, respiratory syncytial virus, and parainfluenza viruses I–IV, and the Filoviridae such as Ebola and Marburg viruses. These represent some of the most problematic pathogens extant.

The present invention provides a method of attenuating a virus of the order Mononegavirales, comprising the step of rearranging the virus' gene order by moving a gene away from its wild-type 3' promoter-proximal position site, wherein said gene is an essential limiting factor for genome replication and wherein said gene is placed in the next to last position in the gene order. Preferably, the gene which is an essential limiting factor for genome replication is the nucleocapsid (N) gene. Representative examples of viruses which can be attenuated using this method include a virus of the order Mononegavirales, e.g., a Rhabdovirus, such as rabies virus or vesicular stomatitis virus, a Paramyxovirus, e.g., measles, mumps, parainfluenza virus or respiratory syncytial virus (human and bovine), or a Filovirus, e.g., Ebola virus or Marburg virus.

The present invention also provides a method of making an attenuated virus useful for a vaccine, comprising the steps of rearranging said virus' gene order by moving a gene away from its wild-type 3' promoter proximal position site, wherein a gene which is an essential limiting factor for genome replication is placed in the next to last position in the gene order; and placing a gene coding for an immune response-inducing antigen in the position closest to the 3' end of the gene order. Preferably, the gene which is an essential limiting factor for genome replication is the nucleocapsid (N) gene. Representative examples of viruses which can be attenuated using this method include a virus of the order Mononegavirales, e.g., a Rhabdovirus such as rabies virus or vesicular stomatitis virus, a Paramyxovirus, e.g., measles, mumps, parainfluenza virus or respiratory syncytial virus (human and bovine), or a Filovirus, e.g., Ebola virus or Marburg virus. In this method of the present invention, the gene coding for an immune response inducing antigen may be the attachment glycoprotein (G) gene, a fusion gene or the hemagglutinin/neuraminadase gene. A person having ordinary skill in this art would be able to readily substitute suitable immune response-inducing antigens. Preferably, the virus useful for a vaccine is attenuated such that the lethal dose and the protective dose of the virus differ by about 1000 fold.

In separate embodiments, the present invention also provides for attenuated viruses using the method of the present invention. The present invention also provides a method of attenuating a virus of the order Mononegavirales, comprising the step of rearranging said virus' gene order by moving a gene away from its wild-type position.

In accordance with the present invention, there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach,"0 Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA molecule. An "exon" is an expressed sequence transcribed from the gene locus, whereas an "intron" is a non-expressed sequence that is from the gene locus.

Transcriptional and translational control sequences are regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a regulatory region capable of binding RNA polymerase in a cell and initiating transcription of a downstream (3' direction) coding sequence. For purposes of definition, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to a n oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA or RNA molecule or gene of the present invention can be used to transform a host using any of the techniques commonly known to those of ordinary skill in the art. One preferred embodiment is the use of a vectors containing coding sequences for the RNA molecules or cDNA molecules of the present invention for purposes of transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of the gene in transgenic systems, in accordance with conventional Southern hybridization techniques known to those of ordinary skill in the art. Both the Northern blot and Southern blot use a hybridization probe, e.g. radiolabelled cDNA, either containing the full-length, single stranded DNA or a fragment of that DNA sequence at least 20 (preferably at least 30, more preferably at least 50, and most preferably at least 100 consecutive nucleotides in length). The DNA hybridization probe can be labelled by any of the many different methods known to those skilled in this art. Alternatively, the label may be incorporated directly into the RNA or protein molecule by many different methods known to those of skill in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, the term "attenuation" is defined as either a genetic mechanism involving premature termination of transcription used to regulate expression of a gene, or immunologically, the process whereby a pathogenic microorganism loses its virulence.

As used herein, the term "lethal dose" is defined as the amount of virus inoculum required to confer lethality on the host.

As used herein, the term "protective dose" is defined as the amount of virus inoculum that produces a sufficient immune response towards the virus without resulting in lethality.

As used herein, the term "rearrangement" is defined as the reordering of the genes within the viral genome, such that the gene and the intergenic regions remain wild-type and only the order with respect to the 3' terminus is altered.

As used herein, the term "negative strand RNA virus" is defined as a classification of RNA viruses in which the viral genome comprises the negative strand of an RNA molecule.

The following examples are given for the purpose of illustrating various embodiments of the invention and are not meant to limit the present invention in any fashion.

EXAMPLE 1

Viruses and Cells

The San Juan isolate of the Indiana serotype of VSV provided the original template for most of the cDNA clones used herein. However, the gene encoding the G protein was originally derived from the Orsay isolate of VSV Indiana (Whelan et al, 1995). Baby hamster kidney (BHK-21) cells were used to recover viruses from cDNAs and for single step growth experiments and radioisotopic labeling of RNAs and proteins. African green monkey kidney (BSC-1 and BSC-40) cells were used for plaque assays.

EXAMPLE 2

Plasmid Construction and Recovery of Infectious Viruses

Figure 2:
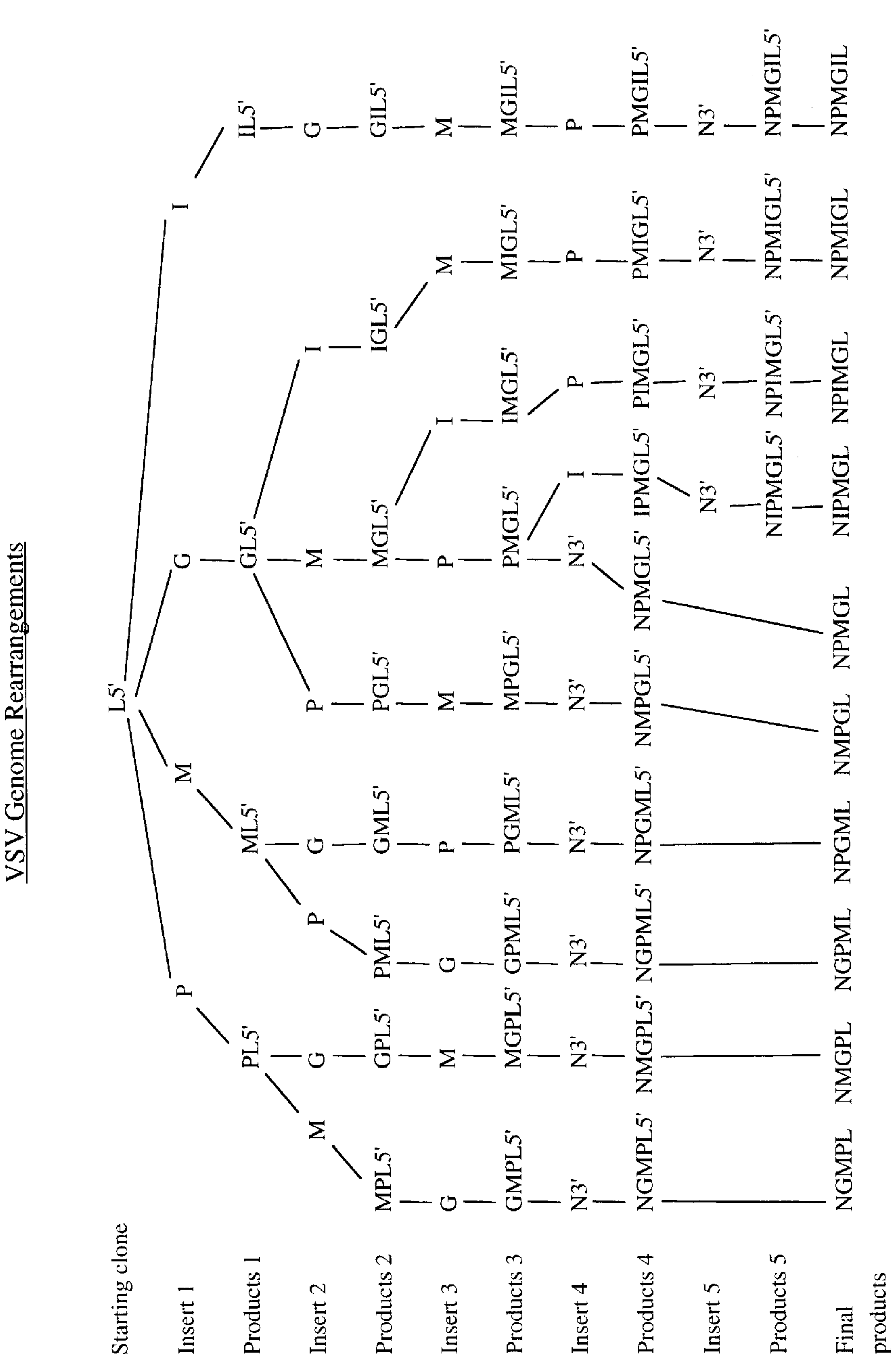
FIG. 2 shows the stepwise procedure for generation of rearranged VSV genomic cDNAs.
Figure 3B:
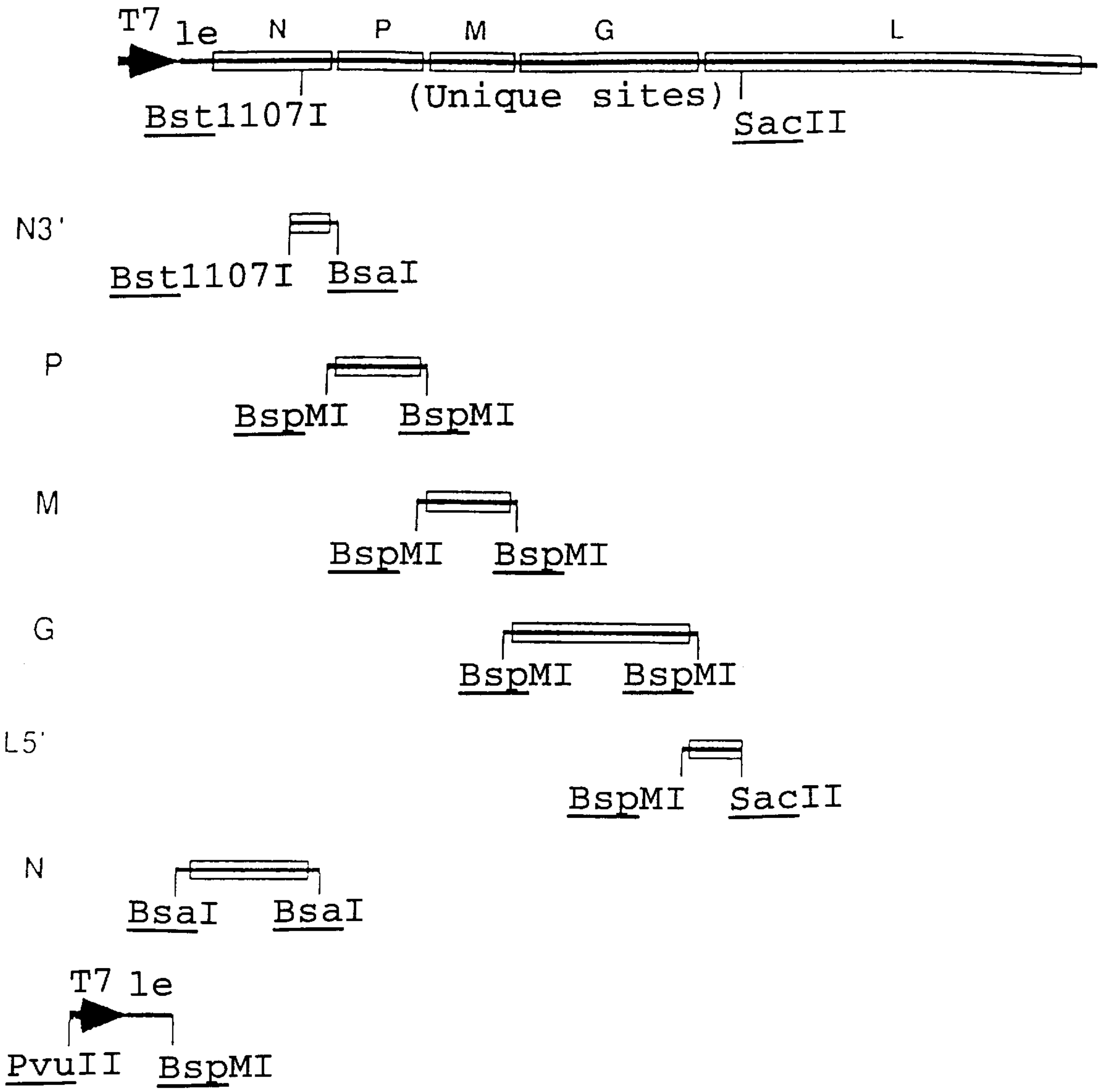
FIG. 3B shows fragments of VSV genome cloned for gene order rearrangement.
Figure 4:
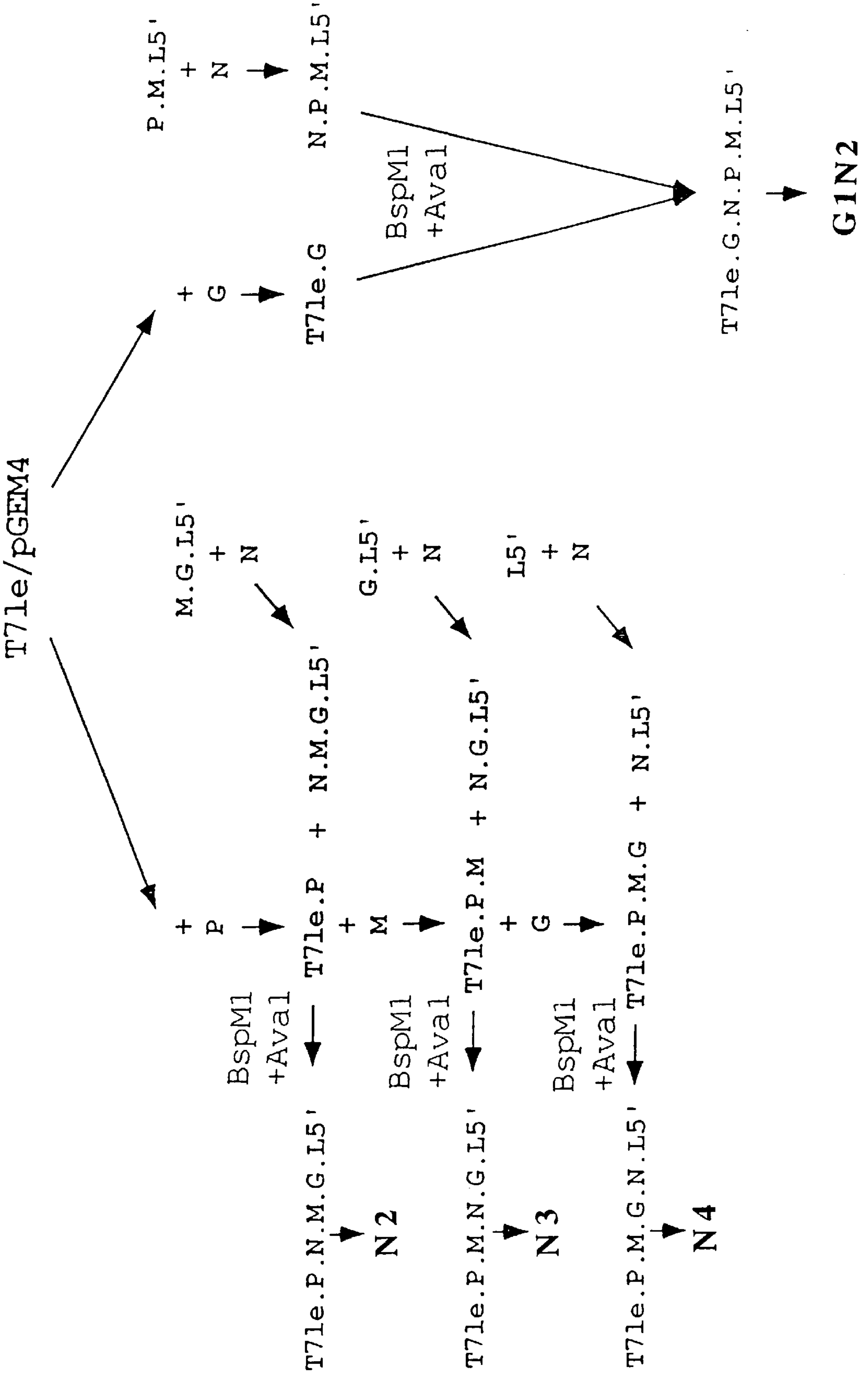
FIG. 4 shows the strategy for construction of rearranged genomes N2, N3, N4 and G1N2.

Each of the five genes of VSV is flanked by a common sequence of eighteen nucleotides. Thus, it was possible to construct individual molecular clones from which DNA fragments precisely encompassing each gene could be released by digestion with an appropriate restriction endonuclease. Restriction endonucleases that cut at sites remote from their recognition sequences were used to create gene segments having cohesive ends that corresponded to the same four nucleotides (ACAG) of the conserved intercistronic regions. In this way, the DNA segments that encompassed each of the five genes could be reassembled in any desired order to create a family of DNA plasmids whose nucleotide sequences corresponded precisely to that of wild-type VSV, except for the fact that their genes were rearranged. A diagram of the steps involved in the construction of the rearranged virus genomes N1 (wt), GMP, MGP, PGM, GPM, MPG, N2, N3, N4, G1N2 and G1N4 is shown in FIGS. 2, 3 and 4.

Infectious viruses were recovered from these DNA plasmids by methods described (Whelan et al., 1995). Briefly, BHK cells were infected with the vaccinia virus recombinant that expresses T7 RNA polymerase, VTF7-3, (Fuerst et al., 1986) and cotransfected with one of the rearranged cDNA plasmids and the three support plasmids that express the N, P and L proteins required for RNA encapsidation and replication. infectious viruses were recovered from the supernatant of transfected cells, amplified by low-multiplicity passage on BHK-21 cells, and filtered through 0.2 mm filters to remove contaminating VTF7-3. The gene orders of the recovered viruses were verified by amplifying the rearranged portions of the viral genomes using reverse transcription and polymerase chain reaction (PCR) followed by restriction enzyme analysis with a set of enzymes which distinguished the rearranged gene orders (FIG. 5).

EXAMPLE 3

Single-cycle Virus Replication

Monolayer cultures of $10^{6}$ BHK-21, BSC-40 or BSC-1 cells were infected with individual viruses at an input multiplicity of 3. Following a one hour adsorption period, the inoculum was removed, cultures were washed twice, fresh media was added and cultures were incubated at 31° C. or 37° C. Samples were harvested at the indicated intervals over a 36 hour period and viral replication quantitated by plaque assay on confluent monolayers of BSC-40 cells.

EXAMPLE 4

Analysis of Viral RNA and Protein Synthesis

Confluent monolayer cultures of BHK-21 cells were infected with individual viruses at an input multiplicity of 5 pfu per cell and given a one hour adsorption period. For analysis of viral RNA synthesis, cultures were treated with actinomycin D (5 μg/ml) at 1.5 hours post-infection for 30 minutes prior to addition of [$^3$H]-uridine (30 μCi/ml) for a 2 or 4 hour labeling period. Cells were harvested, cytoplasmic extracts prepared and RNA analyzed on 1.75% agarose-urea gels as described (Pattnaik and Wertz, 1990). Protein synthesis was analyzed at four hours post-infection by addition of [$^{35}$S]-methionine (40 μCi/ml) for a 30 minute labeling period following a 30 minute incubation in methionine free media. Cytoplasmic extracts were prepared and proteins analyzed on 10% polyacrylamide gels as described previously (Pattnaik and Wertz, 1990). Individual RNAs or proteins were quantitated by densitometric analysis of autoracliographs using a Howteck Scanmaster 3 with Pdi Quantity One software and molar ratios were subsequently calculated.

EXAMPLE 5

Virulence in Mice

The lethality of individual viruses was measured in male Swiss-Webster mice, 3–4 weeks old, obtained from Taconic Farms. Groups of 5–6 lightly anesthetized (Ketamine/Xylazine) animals were inoculated with diluent (PBS) or with serial ten-fold dilutions of individual viruses by either the intracranial route in a volume of 30 μl or by the intranasal route in a volume of 15 μl. Animals were observed daily and the 50% lethal dose ($LD_{50}$) for each virus was calculated by the method of Reed and Muench (1938).

EXAMPLE 6

Protection of Mice

Groups of control mice inoculated with diluent or inoculated intranasally with non-lethal doses of individual viruses were monitored by tail bleeds for neutralizing serum antibody production. On day 14 post-inoculation, mice were challenged with $1.3\times10^6$ pfu of wild-type virus (designated N1) administered intranasally in 15 μl while under light anesthesia as above. Challenged animals were observed for 21 days.

EXAMPLE 7

A General Approach to Rearranging the Genes of the Mononegavirales

To rearrange the genes of VSV without introducing any other changes into the viral genome, the polymerase chain reaction (PCR) was used to construct individual cDNA clones of the N, P, M, and G genes flanked by sites for restriction enzymes that cut outside their recognition sequences. To flank the P, M, and G genes, BspM1 sites were used, whereas to flank the N gene, Bsa1 sites were used (N contains an internal BspM1 site). PCR primers were designed to position these restriction sites so that the four-base cohesive ends left after endonuclease digestion corresponded to the ACAG sequence of the conserved 5' AACAG . . . 3' that occurs at the start of each VSV mRNA (see also FIG. 3A). For example:

5' . . . ACCTGCACTA<u>ACAG</u> . . . AAAAAAACTA <u>ACAG</u>AGATGCAGGT . . . 3'

(SEQ ID No. 1), where the VSV sequence, written in the positive sense, is in italics, the BspM1 recognition sites are in bold letters, and the four-base cohesive ends left by BspM1 digestion are underlined. In this way, the four genes, together with their respective intergenic junctions, were recovered on individual DNA fragments that had compatible cohesive termini (FIGS. 3A and 3B). The only deliberate departure from the wild-type sequence was that the untranscribed intergenic dinucleotide was made 5'-CT-3' at all junctions, including that following the P gene where the wild-type sequence is 5'-GT-3'. This mutation is apparently silent (Barr et al., 1997). To circumvent the effect of spurious mutations arising during PCR, the termini of the cloned genes were sequenced and their interiors were replaced with corresponding DNA fragments from the infectious clone.

Two other starting plasmids were required to reconstruct the rearranged full-length clones: one contained a bacteriophage T7 promoter followed by the VSV leader sequence, with a unique BspM1 site positioned to cut within the 5' (A)ACAG at the start of the N gene:

5' . . . GAAACTTTA<u>ACAG</u>TAATGCAGGT . . . 3' (SEQ ID No. 2).

(the type faces/fonts are as described above). The other plasmid contained the first 420 nucleotides of the L gene and had a unique BspM1 site positioned to cut within the same sequence at the start of L:

5' . . . ACCTGCACTA<u>ACAG</u>CAATCATG . . . 3' (SEQ ID No. 3).

The N, P, M and G gene fragments were ligated unidirectionally into the unique BspM1 sites of these plasmids to rebuild the viral genome in a stepwise manner from either the 3' or the 5' end. Insertion of each gene recreated a wild-type intergenic junction and left a unique BspM1 site to receive the next gene.

The final step of plasmid construction was to add a DNA fragment from the infectious clone that encompassed the remaining 6 kb of the L gene, the 5' end of the viral genome, and the ribozyme and T7 terminator that are needed for the intracellular synthesis of replication-competent transcripts (Pattnaik et al., 1992). This approach can be applied to any of the Mononegavirales which have conserved sequences at their intergenic junctions. The rearranged gene orders that were created in this manner are shown in FIG. 1. To validate this cloning strategy and to verify that the individual genes encoded functional proteins, a plasmid that contained the wild-type genome was created in parallel with the rearranged cDNA clones. Virus recovered from this plasmid was used as the wild-type (N1, see FIG. 1). In all cases, the conserved 23 nucleotide intergenic region was maintained between genes.

EXAMPLE 8

Generation of Viruses with Rearranged Genomes

Initial rearrangements of the cDNA of the genome of VSV were conservative, in light of the highly conserved nature of the genomes of all viruses in the family Mononegavirales, and the knowledge that precise molar ratios of the VSV nucleocapsid (N) protein, phosphoprotein (P) and RNA polymerase (L) protein are required for replication. The 3' most gene, N, and the 5' most gene, L, were originally maintained in their natural positions and the three central genes of VSV, the P, M and G genes, were rearranged in all possible combinations to generate the 6 genome orders (N1 (wt), GMP, MGP, PGM, GPM and MPG) as shown in FIG. 1. The wild-type gene order, N1, was generated as described above to serve as a test that all of the cDNA elements were functional. Each of the cDNAs was constructed in a specialized T7 expression plasmid designed to generate RNAs having precise 5' and 3' termini (Pattnaik et al, 1992).

The ability of the rearranged cDNAs to generate a functional RNA genome was demonstrated by transfecting each of the six rearranged cDNAs into BHK cells infected with vaccinia virus expressing the T7 polymerase (Fuerst et al., 1986) concomitantly with cDNA clones encoding the VSV N, P, and L proteins to encapsidate the RNA transcribed from the cDNA clones and to form functional ribonucleocapsids as described (Whelan et al., 1995). Virus was recovered with varying efficiency from all six of the cDNA constructs and amplified in the presence of cytosine arabinoside (25 μg/ml) following filtration through 0.2 μm filters to remove the recombinant vaccinia virus used to express the T7 polymerase required for transcription of the cDNAs to yield RNA virus.

EXAMPLE 9

Figure 5A:
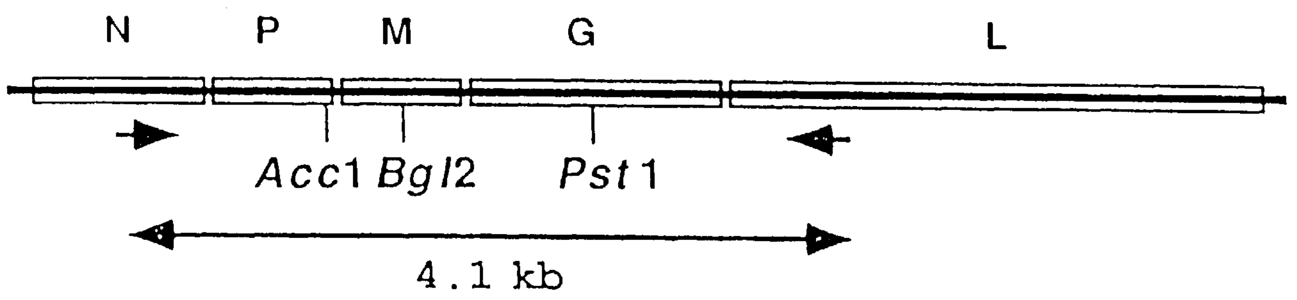
FIG. 5A shows the restriction map of enzymes used to determine gene order of cDNAs prepared by reverse transcription and PCR of genomes of rearranged viruses. The three restriction enzymes shown discriminate between all 6 genome arrangements for N1, GMP, MGP, PGM, GPM and MPG.
Figure 5B:
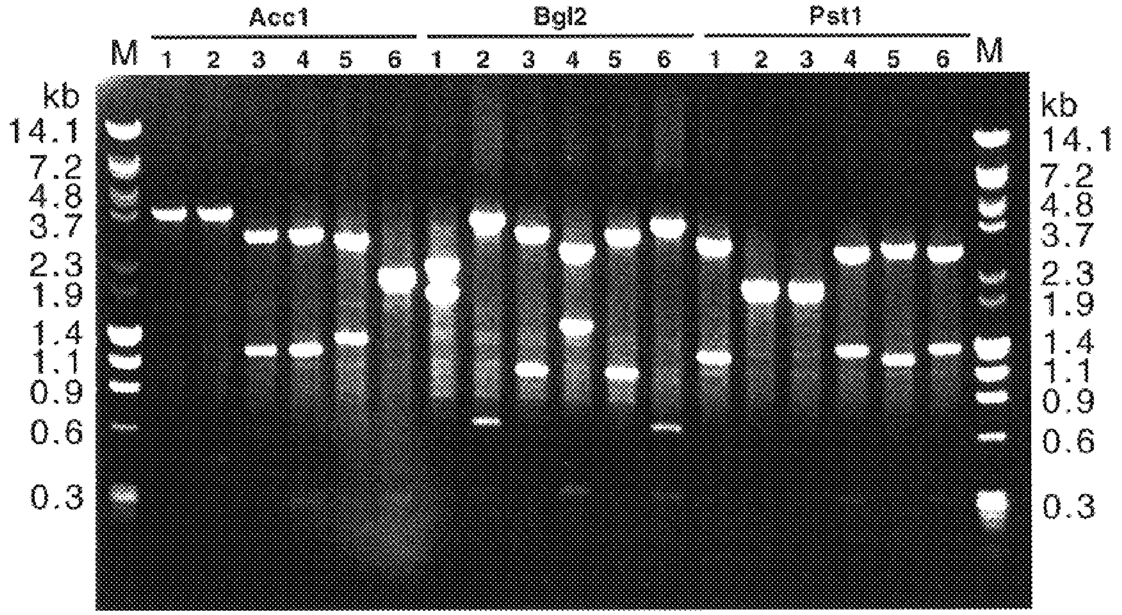
FIG. 5B shows the restriction enzyme cleavage patterns of cDNAs derived from the genomes of rearranged viruses N1, GMP, MGP, PGM, GPM and MPG.

The Gene Order of the Recovered RNA Viruses Reflects that of the cDNA from Which they were Generated Genomic RNA was isolated from each of the recovered virus populations and the organization of the genes analyzed. Reverse transcription of the RNA, followed by PCR amplification, was used to generate cDNAs from each of the recovered genomes. As shown in FIG. 5A, the use of three restriction enzymes was sufficient to generate specific fragment patterns that discriminated all of the 6 possible genomes. FIG. 5B shows restriction enzyme analysis of cDNAs generated by reverse transcription and PCR of the RNA from each recovered virus. These data confirm that the RNA genomes of all of the recovered viruses reflected exactly the arranged order of the genes on the input cDNA.

EXAMPLE 10

RNA Synthesis by Recovered Viruses

Figure 6:
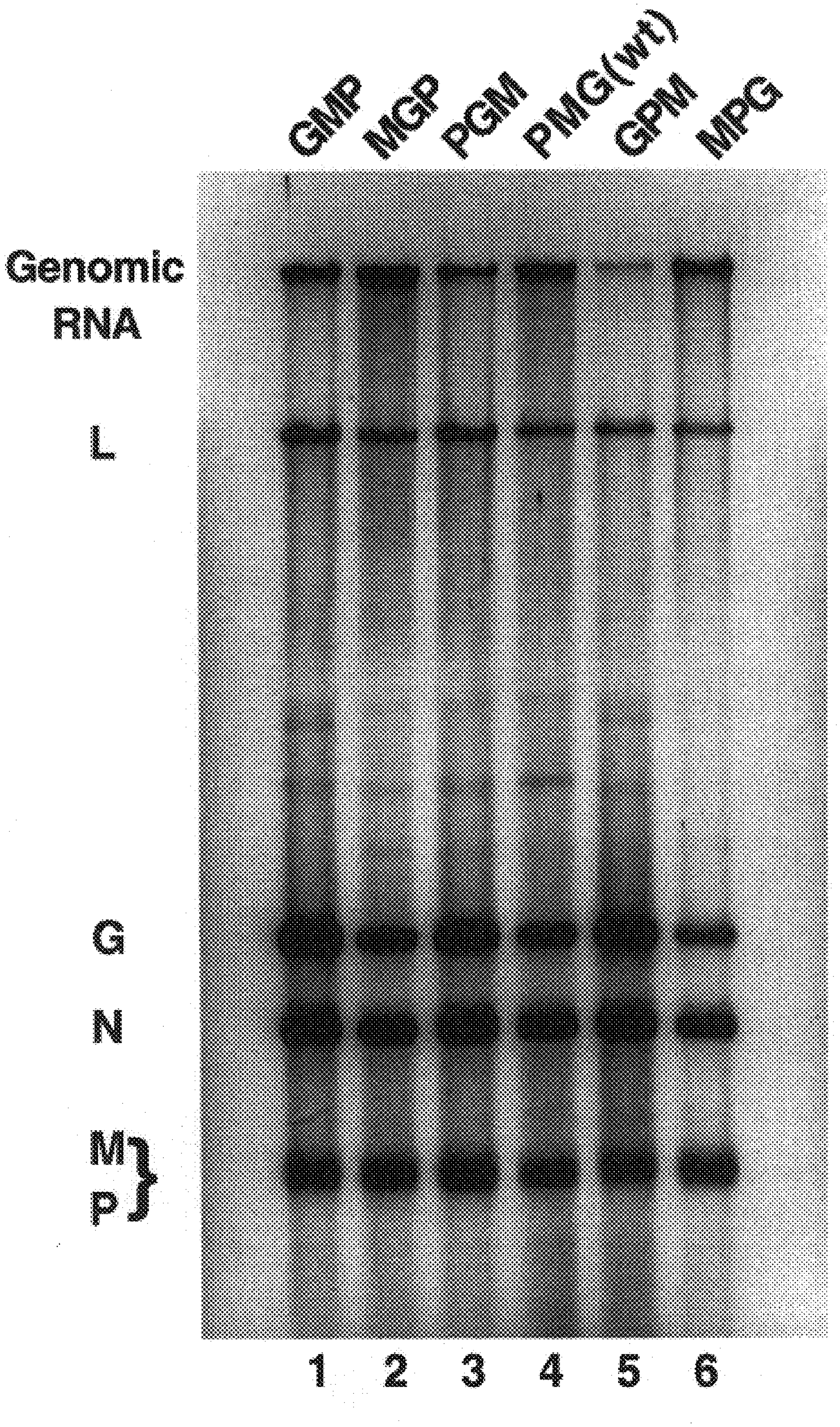
FIG. 6 shows the viral specific RNA synthesized in BHK-21 cells infected with rearranged viruses GMP, MGP, PGM, PMG (wt), GPM and MPG. Cells were infected with each virus at a MOI of 2 pfu and labeled with [$^3$H]-uridine at 2–6 hours postinfection in the presence of 5 $\mu$g/ml actinomycin D.

The pattern of viral specific RNA synthesis for each recovered virus (N1, GMP, MGP, PGM, GPM and MPG) was analyzed in BHK cells infected at a multiplicity of 10 pfu per cell. RNA was labeled from 2 to 4 hours postinfection with [$^3$H]-uridine in the presence of actinomycin D. All of the recovered viruses synthesized intact virion RNA, as well as the 5 VSV specific mRNAs: the N, P, M, G and L mRNAs (FIG. 6). Despite the fact that the gene specific sequences flanking the intercistronic junctions were different in the rearranged genomes, the intercistronic junctions all functioned normally as evidenced by the specific pattern of RNA products shown in FIG. 6. The P and M RNAs comigrate due to their similar sizes (814 and 831 nucleotides, respectively). Therefore, to ascertain that the P and M mRNAs were both synthesized, total RNA from the above infections with N1, GMP, MGP, PGM, GPM and MPG were incubated with RNAse H following annealing to a negative sense oligonucleotide specific for the center of the P mRNA. RNAse H specifically cleaved the P mRNA in the presence of the oligonucleotide but not in its absence, and gel analysis revealed the presence of the M mRNA and the faster migrating, cleaved halves of the P specific mRNAs for all 6 rearranged viruses. This confirms synthesis of both the P and M mRNAs for each virus.

The pattern of RNA synthesis for each of the recovered viruses varied. Rearranged viruses GMP and GPM, for example, which have the G gene moved forward in the gene order to immediately behind the N gene, synthesized G mRNA at a significantly higher molar ratio than that seen in the wild-type gene arrangement (FIG. 6, compare lanes GMP and GPM with lane PMG (wt)).

EXAMPLE 11

Protein Expression by Viruses with Rearranged Genomes

The pattern of proteins synthesized by each rearranged virus was analyzed in BHK-21 cells by metabolic labeling with [$^{35}$S]-methionine. Each of the rearranged viruses synthesized the five VSV proteins: the N, P, M, G and L proteins, as did the wild-type virus, PMG (FIG. 7). The levels of expression of the various proteins varied in each of the virus infections. For example, GMP and MGP have the P gene moved to the next to last position in the gene order. Lowered levels of P protein were synthesized by GMP and MGP in comparison to PGM and the wild-type PMG, where P is second in the gene order. Intermediate levels of P are synthesized in GPM and MPG, where the P gene is third in the order. Similarly, the levels of G protein synthesized by GMP and GPM were increased over those of the wild-type PMG and MPG, where G is in the wild-type position next to the last gene, L. The level of M protein expression was also increased when its gene was moved to the second position as in MGP and MPG, as compared with PGM and GPM in which the gene encoding the M protein is in the next to last position.

EXAMPLE 12

Molar Ratios of Proteins Expressed from Rearranged Viruses

Figure 8A:
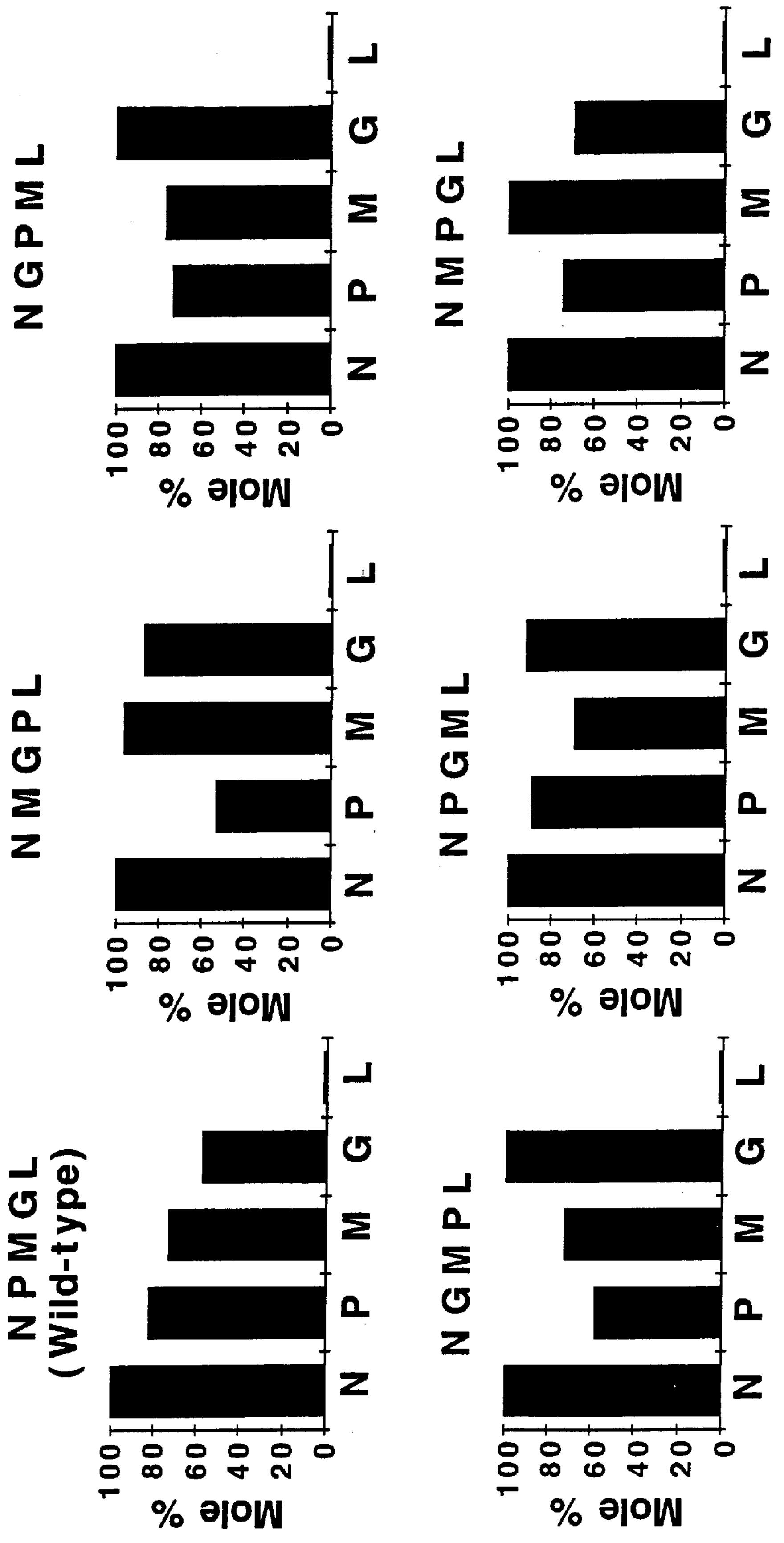
Figure 8B:
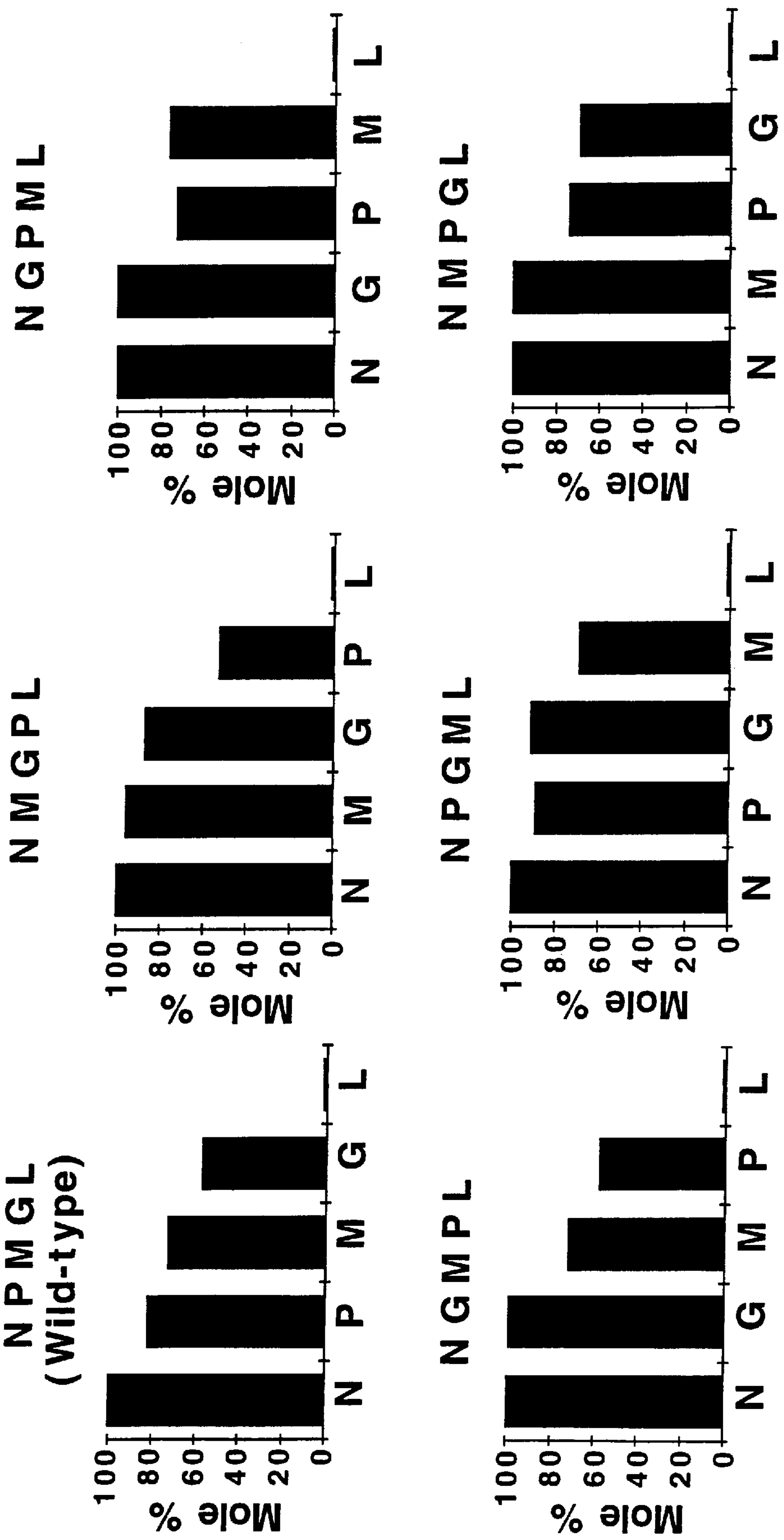

The molar ratios of the proteins expressed from each rearranged variant virus were analyzed by densitometric scanning of autoradiograms. FIG. 8A shows that the molar ratios of the individual proteins calculated, relative to that of the N protein, varied according to the position of their respective gene from the 3' end of the genome. For example, when the P and G gene positions were exchanged, as in GMP to make G second in the order and P next to last, their relative levels of expression were exchanged compared to that seen in the wild-type virus. When the molar ratios were plotted according to the actual gene order (FIG. 8B), the levels of expression decreased relative to the distance of the gene from the 3' end of the genome. These data show that the position of the gene determines the level of expression, even when rearranged from wild-type.

EXAMPLE 13

Effect of Genome Rearrangements on Growth in Cell Culture

The rearranged viruses were compared for their ability to replicate under the conditions of plaque formation and single-cycle growth. Although some of the viruses, such as MGP and MPG, were indistinguishable from the N1 wild-type virus (gene order PMG) in these assays, others, such as GMP, GPM, and PGM, formed significantly smaller plaques than the wild-type on monolayers of BSC-1 cells (Table 1). Moreover, GMP plaques ceased to grow after 24 h when those of the wild-type virus and the other variants were still increasing in size (Table 1). The impaired replication of GMP, GPM, and PGM was also demonstrated during single-cycle growth on BSC-1 cells, and the replication of GPM and GMP appeared to be delayed by 1–2 h relative to the other viruses (FIG. 9). At 17 h post-infection, the incremental yields of the variants averaged over three independent growths and expressed as percentages of the wild-type were: MGP=107%; MPG=51%; GMP=23%; PGM=21%; and GPM=1.6%.

TABLE 1

| | Plaque diameter (mean ± S.E.)[a] | |
|---|---|---|
| Virus | 24 h | 30 h |
| N1 | 4.02 ± 0.12 | 4.81 ± 0.19 |
| GMP | 3.08 ± 0.17 | 3.10 ± 0.18 |
| MGP | 3.96 ± 0.19 | 4.97 ± 0.18 |
| PGM | 3.36 ± 0.12 | 3.86 ± 0.14 |

TABLE 1-continued

| Plaque diameter (mean ± S.E.)[a] | | |
|---|---|---|
| Virus | 24 h | 30 h |
| GPM | 2.26 ± 0.09 | 3.16 ± 0.13 |
| MPG | 3.85 ± 0.18 | 5.43 ± 0.17 |

[a]Plaque diameters were measured from photographs taken at approximately two-fold magnification of groups of 50 (24 h) or 70 (30 h) viral plaques formed at 37° C. on monolayers of BSC-1 cells.

EXAMPLE 14

Effect of Genome Rearrangements on Lethality in Mice

Intracerebral or intranasal inoculation of wild-type VSV into mice causes fatal encephalitis. Since 1938, when Sabin and Olitsky first described the neuropathology and comparative susceptibility of mice to encephalitis as a function of age and route of inoculation, young mice have served as a convenient and sensitive small animal model for comparing the lethality of VSV and its mutants (Lyles et al., 1996; Ferran and Lucas-Lenard, 1997). The pathogenesis of the variant viruses in mice was therefore examined.

Intranasal inoculation of wild-type VSV into 3–4 week old mice causes encephalitis, paralysis and death after 7–11 days (Lyles et al., 1996), with the $LD_{50}$ dose being about 10 pfu. The virulence of the variant viruses was compared by inoculating groups of mice intranasally and observing them twice daily. The results of a representative experiment are shown in FIG. 10. The left panels show the percent mortality induced by different doses of the rearranged viruses, while the right panels show the time of appearance of symptoms and death at a dose of 100 pfu per mouse. The wild-type infected animals first appeared sick at 6 d post-inoculation, rapidly became paralyzed, and died within two weeks. The variant viruses required 3- to 10-fold less virus for an $LD_{50}$ dose (see also Table 2). The rearranged viruses GMP and MGP elicited reproducibly faster pathogenesis, with symptoms developing 24–36 h earlier than in wild-type infected animals (FIG. 10). This difference in rate was apparent even when inocula of equivalent lethality were compared. In general, the paralysis that is typical of infection with wild-type VSV was less apparent with the rearranged viruses, but no evidence was detected of persistent nervous system disease such as that produced by some M protein mutants (Barr et al., 1997).

Virulence in mice contrasted sharply with the cell culture phenotypes of the rearranged viruses (Table 2). Of the three recombinants whose replication in cell culture was compromised (GMP, PGM, and GPM), one (GMP) had a ten-fold lower $LD_{50}$ than the wild-type and induced accelerated pathogenesis in mice. The other two (PGM and GPM) also had ten-fold lower $LD_{50}$ values than the wild-type virus but elicited symptoms with similar kinetics as the wild-type. Conversely, of the two variants (MGP and MPG) that replicated to wild-type titers in cell culture, one (MPG) more closely resembled the wild-type in its virulence, whereas the other (MGP) was more virulent. This lack of correlation between the behavior of viruses in cell culture and their properties in animals is a familiar observation among different animal viruses, but it was particularly striking in this context where the only differences between the viruses were the relative levels of wild-type proteins that they expressed.

TABLE 2

| Summary of properties of variant viruses | | | | |
|---|---|---|---|---|
| Virus | Relative plaque size[a] | Relative burst size[b] | $LD_{50}$ value[c] | Onset of sympt[d] |
| N1 (wt) | (1.00) | (1.00) | 11 | 6.0 d |
| GMP | 0.64 | 0.23 | 1 | 4.5 d |
| MGP | 1.03 | 1.07 | 1 | 5.5 d |
| PGM | 0.80 | 0.21 | 1 | 5.5 d |
| GPM | 0.66 | 0.016 | 1 | 5.5 d |
| MPG | 1.13 | 0.51 | 3 | 5.5 d |

[a]Measured at 30 h post-infection.
[b]Measured at 17 h post-infection (see FIG. 9).
[c]Pfu per mouse inoculated intranasally.
[d]Days after intranasal inoculation of 100 pfu per mouse (see FIG. 10).

EXAMPLE 15

Effect of Severe Rearrangements on Recovery of Viable Virus

Encouraged by the relative tolerance that VSV exhibited for rearrangement of the three internal genes based on recovery of infectious virus, further rearrangements were made that altered the position of the gene for the nucleocapsid protein, N. The N protein is required in stoichiometric quantities to support encapsidation of nascent genomic RNA during RNA replication (Patton et al., 1984). RNA replication is dependent on constant synthesis of the N protein, and inhibition of N protein synthesis results in cessation of replication. If the level of N protein synthesis were lowered by moving the N gene progressively away from its promoter proximal site (and thus lowering the level of N gene expression), it would therefore result in lowered levels of genomic replication. As such, the genome of VSV was altered at the cDNA level by moving the N gene from the 3' most position, which results in synthesis of the largest amount of N mRNA, to each sequential internal position as shown in FIG. 1 to create N2 (PNMGL), N3 (PMNGL), and N4 (PMGNL). N1 corresponds to the wild-type arrangment. A fourth and fifth variation, in which the G gene was moved from next to last in the order and placed in front of the N gene, was also generated (FIG. 1). This results in G1N2 (GNPML), as well as G1N4 (GPMNL), where the position of the G and N genes were exchanged.

The cDNAs for N1–N4, G1N2 and G1N4 were transfected into cells as described above and analyzed for the ability to generate viable virus. Virus was recovered with comparative ease from N2, N3 and G1N2. Virus was not recovered from N4 and G1N4, even with repeated trials using standard transfection conditions at 37° C. Virus corresponding to N4 and G1N4 was recovered by lowering the temperature of the transfections and subsequent passages to 31° C.

EXAMPLE 16

RNA Synthesis by Viruses with N Gene Rearrangements

Moving the N gene sequentially down the genome had a marked effect on the level of replication and N mRNA synthesis (FIG. 11). The level of N mRNA synthesis decreased substantially from wild-type levels as the N gene was moved successively away from the promoter in viruses N2, N3 and N4 (36%, 6% and 3% of wild-type, respectively; FIG. 11). Consistent with this, an increase in the amount of G mRNA was observed with virus N4, in which the G gene was moved one position closer to the promoter as the N gene replaced it as next to last in the gene order (FIG. 11). The amount of genomic RNA replication of N2, N3 and N4 declined relative to wild-type (50%, 28% and 4%, respectively; FIG. 11), concomitant with the lowered expression of the N gene, as predicted if N protein synthesis was limiting for replication. The overall level of transcription was reduced also as the N gene was moved progressively promoter distal, presumably as a secondary effect due to the lowered number of genomic templates.

EXAMPLE 17

Protein Synthesis of Viruses with the N Gene Rearranged

All five of the VSV proteins were expressed in cells infected with the rearranged viruses and they all co-migrated with those of the wild-type virus. However, N protein synthesis declined as its gene was moved away from the 3' position. The data presented in FIG. 12 show how the molar amounts of the proteins decrease as a function of their distance from the 3' terminus in the wild-type virus N1. When the N gene w as translocated, the data in FIG. 12 show that the molar ratios of the N protein relative to the phosphoprotein P decreased progressively as the N gene was moved from first to second, third, or fourth in the gene order. These results confirm the predictions from previous analysis of gene expression in VSV and the sequential nature of transcription. Moreover, these data demonstrate directly that the position of a gene determines its level of expression. Examination of the levels of proteins in isolated, mature N1–N4 virions showed that the relative molar ratios of the proteins in mature virus particles remained essentially the same as that of the wild-type virus. However, less overall virus was produced from infections of N2–N4, correlating with the lowered level of genomic RNA replication.

EXAMPLE 18

Replication Ability in Cell Culture

Viruses with the N gene rearrangements replicated progressively less well as the N gene was moved downstream of its normal promoter proximal position. Growth potential was analyzed by single step growth curves. N2 and G1N2 were reduced in viral yields by approximately 15-fold at 37° C.; N3 was reduced by 50 fold and N4 was reduced by 20,000 fold in replication ability as compared to the wild-type virus (FIG. 13). Comparison of virus growth at 31° C. showed a similar progressive decline, however, the effect was less pronounced than at 37° C., and overall, this temperature was more permissive for growth (FIG. 13, inset). At 31° C., N4 replication was reduced approximately 100 fold compared to wild-type. The burst size in pfu per cell for each of the viruses at 31° C. and 37° C., shows that the yield per cell declined in a stepwise manner as the N gene was moved to each successive position down the genome (FIG. 13). The relative plaque sizes of the viruses also varied; plaques of N4 are compared to that of wild-type (<0.5 mm compared to 3 mm in diameter at 42 hours post infection). These data indicate that although the genes of N2, N3 and N4 were wild type, rearrangement of the genes and the subsequent alterations of the protein molar ratios rendered some step of the viral replication process partially temperature sensitive.

EXAMPLE 19

Lethality in Mice

Growth of VSV in mice, neuropathology and susceptibility to encephalitis by intracerebral or intranasal inoculation of wild-type, temperature sensitive or plaque size variant viruses has been described in detail (Sabin and Olitsky, 1937; Shechmeister et al., 1967; Wagner, 1974; Youngner and Wertz, 1968). The lethality of viruses N2, N3 and N4 for mice was examined in comparison with the wild-type virus N1 for both the intracerebral and intranasal routes of inoculation. The amounts of virus required for a lethal dose ($LD_{50}$) by each route is shown in Table 3. By intercerebral inoculation, the $LD_{50}$ dose for each of the viruses was 1 to 5 pfu, although the average time to death was about twice as long with the N4 virus. These data show that when injected directly into the brain, thereby circumventing the majority of ho s t defenses, the rearranged viruses eventually could cause fatal encephalitis.

Intranasal inoculation, by contrast, showed striking differences in the amount of virus required for a lethal dose (Table 3). Whereas the $LD_{50}$ dose for the wild-type virus by IN administration was approximately 10 pfu, the values for N2, N3 and N4 viruses were progressively greater. N2 required 20 fold more virus, N3, 500 fold more virus, and N4 required 3000 fold more virus than wild-type, i.e. 30,000 pfu for the $LD_{50}$. The time to onset of sickness (ruffled fur, lethargy, hind limb paralysis) and extent of death increased progressively compared to wild-type following infection with viruses N2, N3 and N4 (FIG. 14) and the extent of mortality was a function of dose (Table 3). These data show that when administered by a peripheral route, the progressive reduction in virus replication observed in cell culture correlated with a reduced lethality in mice.

TABLE 3

Lethality of wild-type of Rearranged VSV Viruses for Mice

| | $LD_{50}$ Data* pfu/mouse (Average day to death) | |
|---|---|---|
| | Intracranial | Intranasal |
| N1 NPMGL (WT) | 1 (3–6) | 11 (5–10) |
| N2 PNMGL | 5 (3–7) | 250# (9–12) |
| N3 PMNGL | 5 (3–8) | 5,400# (7–9) |
| N4 PMGNL | 1 (4–11) | 30,000 (10–12) |

*The $LD_{50}$ for each route of inoculation was calculated from mortality among groups of 5 to 7 mice inoculated either IC or IN with five serial 10-fold dilutions of virus. Data from a single internally controlled experiment are shown; the duplicate experiments carried out for each route of administration were similar.
#Mortality data for this virus yielded a bell shaped death curve; the $LD_{50}$ dose was calculated from the lower part of the curve. Days to death are shown in parentheses.

EXAMPLE 20

Ability of Rearranged Viruses to Protect Against Wild-type Challenge

The observation that all of the viruses were lethal when inoculated IC indicated that even the most attenuated viruses were able to replicate in mice. This, coupled with the attenuation observed following intranasal administration, raised the possibility that the attenuated viruses might nevertheless be able to elicit a protective immune response. To test this possibility, mice were immunized by IN inoculation with serial ten-fold dilutions of the wild-type N1 or with variant viruses N2, N3 or N4. The surviving animals were challenged 14 days later by IN inoculation with $1.3\times10^6$ pfu of wild-type virus. The percentage of animals surviving the challenge was a function of the immunizing dose in agreement with previous studies (Wagner, 1974). For viruses N2, N3 and N4, 300 pfu per mouse was the lowest dose giving 100% survival; 30 pfu yielded 80–90% survival; 3–6 pfu gave 45–85% survival; and doses below 3–6 pfu per mouse gave results that were not significantly different from those of age matched unimmunized controls (FIG. 15, dotted line in panel A). With the wild-type virus, the lethal dose and the protective dose were close, but in general, 80–85% of animals that survived administration of 3–6 pfu of virus were protected.

Measurement of serum antibody prior to challenge on day 14 showed that despite attenuation for virulence in mice, the level of neutralizing antibody present in the serum of animals immunized with viruses N2, N3 and N4 was higher than that observed in the animals surviving inoculation of 3–6 pfu of wild-type virus and generally increased in a dose dependent manner (FIG. 15B). The lethality of the wild-type virus prevented direct comparison of antibody titers at higher doses, however, the neutralizing antibody titers in animals both vaccinated with viruses N1–N4 and then challenged with $1\times10^6$ pfu of wild-type virus ranged from 1:625 to 1:3125. These data show that despite their attenuation for replication and lethality in animals, the N-rearranged viruses elicited a protective response that was undiminished compared with that of the wild-type virus.

EXAMPLE 21

Organization of Genes to Develop an Optimum Vaccine Virus

The present invention illustrates that gene order in the Mononegavirales determines the level of gene expression. Furthermore, these data show that moving the important Nucleocapsid (N) gene away from its normal 3' promoter proximal position provides a means of generating sequentially more attenuated viruses. The maximal level of attenuation occurs when the N gene is placed next to last in the gene order. The highest level of expression occurs from the 3'-most gene. Therefore, in constructing a vaccine vector that is both attenuated and expresses high levels of the antigen involved in protection, the ideal arrangement is a combination of N4 (PMGNL) or G1N2 (GNPML) or G1N4 (GPMNL). In these constructs, N4 is maximally attenuated and G1N2 yields the greatest levels of the attachment glycoprotein, important for an immune response. Based upon this criteria, G1N4 (GPMNL) should be maximally attenuated and yield the highest levels of G protein.

EXAMPLE 22

A Vaccine Vector Capable of Expressing Additional Foreign Genes so that the Level of the Foreign Gene is Regulated by Position The genome of VSV can accommodate and express additional foreign genes if inserted at intergenic regions and if the conserved gene start, gene end and intergenic regions are maintained (FIG. 16) (Schnell et al., 1996). Additionally, the level of expression of a foreign gene inserted in the VSV genome can be controlled by the position in the genome at which the gene is inserted. A 660 nucleotide sequence of the bacteriophage Phi X174 genome surrounded by the conserved VSV gene start and gene end sequences was inserted into each sequential gene junction of the full length cDNA of the VSV genome in such a manner so as to maintain the conserved intergenic sequences. The gene order of these constructs was respectively: NIP (NIPMGL), PIM (NPIMGL), MIG (NPMIGL), or GIL (NPMGIL) where I represents the (I)nserted foreign gene. Virus was recovered from each of the above-mentioned cDNAs by transfection as described above.

The viruses with the foreign gene sequence inserted a t each position in the genome were each used to infect BHK-21 cells and synthesis of RNAs was analyzed by metabolic labeling with [$^3$H]-uridine in the presence of actinomycin D. VSV genomic RNA and the 5 VSV specific mRNAs were expressed from all of the recovered viruses (FIG. 16). In addition, in all four cases, the synthesis of an mRNA of the size expected from the inserted foreign genetic material was also observed. The level of expression of the foreign gene varied as its position of insertion from the 3' end of the genome. The highest level of expression was from NIP, followed by PIM, MIG and GIL (FIG. 16). Thus, these data show that foreign genes may be inserted into the genome of VSV and that the foreign gene will be expressed if surrounded by the conserved VSV gene start and stop signals. Most importantly, this data shows that the level of expression of the foreign gene is controlled by the position at which the gene is inserted into the genome.

Analysis of the growth potential of each of the viruses expressing a foreign gene showed that the position of the insertion of the foreign gene determined whether or not there was an effect on viral growth. NIP was reduced by 10-fold in viral yields compared to wild-type virus, whereas PIM, MIG and GIL all replicated to levels equivalent to that of wild-type virus. Thus, these data show that insertion of a foreign gene is possible, that it is not lethal to the virus, and that it may, depending on the position of insertion, serve to attenuate replication.

EXAMPLE 23

Summary

The present invention demonstrates that the order of genes in negative strand RNA viruses determines the level of gene expression. The gene order can be rearranged and the levels of expression of the rearranged viral genes reflects their position relative to the 3' promoter of transcription. By rearranging a single gene essential for replication, such as the N (nucleocapsid) gene, to successive positions down the viral genome, it is possible to affect the growth potential in cell culture and the lethality of the virus for mice in a stepwise manner. Thus, these data demonstrate a means of attenuating these viruses in a stepwise manner. Attenuated viruses, such as N4 (PMGNL), are such that the lethal dose and the protective dose of the virus differ by over 1000-fold, an attribute desirable for an attenuated vaccine candidate.

In addition, the present invention demonstrates that one may insert foreign genes into the genome of the negative strand virus, and recover infectious virus which expresses the foreign gene. The level of expression of the foreign gene can be controlled by the position in the genome relative to the 3' end at which the gene is inserted. The ability of these viruses to accommodate foreign material is most likely due to the fact that they possess helical ribonucleocapsids, such that the nucleocapsid and the virus both become larger as the size of the genome is increased. No limit on the amount of foreign material that may be inserted has been reached.

The methodology of the present invention can be used to develop attenuated viruses for vaccines, and such methodology is applicable to all members of the family Mononegavirales based upon the close similarity of the genome organization and mechanism for control of gene expression for the members of the family. The Mononegavirales include the Rhabdoviruses, such as rabies, the Paramyxoviruses, such as measles, parainfluenzaviruses, and respiratory syncytial virus, and the Filoviruses such as Ebola and Marburg.

The following references were cited herein:

Ball, L. A. 1992. *J. Virol.* 66, 2335–2345.

Ball, and White. 1976. *Proc. Natl. Acad. Sci.* USA 73, 442–446.

Barr, J. N. et al. 1997. *J. Virology* 71, 1797–1801.

Domingo, E. et al. 1996. *The FASEB Journal* 10, 859–864.

Ferran, M. and J. M. Lucas-Lenard. 1997. *J. Virol.* 71, 371–377.

Fuerst, et al. 1986. *Proc. Natl. Acad. Sci.* USA 83, 8122–8126.

Iverson, L. and J. Rose. 1981. *Cell* 23, 477–484.

Lyles, D. S. et al. 1996. *Virology* 217, 76–87.

Pattnaik, A. K. and G. W. Wertz. 1990. *J. Virol.* 64, 2948–2957.

Pattnaik, A. K. et al. 1992. *Cell* 69, 1011–1020.

Pringle, C. R. et al. 1981. *J. Virol.* 39, 377.

Reed, E. J. and H. Muench. 1938. *Am. J. Hyg.* 27, 493–497.

Sabin, A. and P. Olitsky. 1938. *J. Exp. Med.* 67, 201–227.

Schnell, M. J. et al. 1996. *J. of Virol.* 70, 2318–2323.

Shechmeister, et al. 1967. *Arch. Ges. Virusforsch.* 21, 127–132.

Villareal, L. P. et al. 1976. *Biochem.* 15, 1663.

Wagner, R. 1974. *Infection and Immunity* 10, 309–315.

Whelan, et al. 1995. *Proc. Natl. Acad. Sci.* USA 92, 8388–8392.

Wimmer, E. et al. 1993. *Ann. Rev. Genetics.* 27, 353–436.

Youngner, J. S. and G. Wertz. 1968. *J. Virol.* 2, 1360–1361.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and/or specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of attenuating a virus of the order Mononegavirales, comprising the step of:

rearranging said virus' gene order by moving said virus' nucleocapsid (N) gene away from its wild-type 3' promoter proximal position site, wherein said gene is an essential limiting factor for genome replication and wherein said gene is placed in the next to last position in the gene order.

2. The method of claim 1, wherein said virus of the order Mononegavirales is a Rhabdovirus.

3. The method of claim 2, wherein said Rhabdovirus is selected from the group consisting of rabies virus and vesicular stomatitis virus.

4. The method of claim 1, wherein said virus of the order Mononegavirales is a Paramyxovirus.

5. The method of claim 4, wherein said Paramyxovirus is selected from the group consisting of measles, mumps, parainfluenza virus and respiratory syncytial virus.

6. The method of claim 5, wherein said respiratory syncytial virus is selected from the group consisting of human respiratory syncytial virus and bovine respiratory syncytial virus.

7. The method of claim 1, wherein said virus of the order Mononegavirales is a Filovirus.

8. The method of claim 7, wherein said Filovirus is Ebola virus.

9. The method of claim 7, wherein said Filovirus is Marburg virus.

10. A virus attenuated according to the method of claim 1.

11. A method of attenuating a virus of the order Mononegavirales, comprising the step of:

rearranging said virus' gene order by moving said virus' nucleocapsid (N) gene away from its wild-type position.

* * * * *

SEQUENCE LISTING

```
(1) GENERAL INFORMATION:

   (iii) NUMBER OF SEQUENCES:  12

(2) INFORMATION FOR SEQ ID NO:1:

     (i) SEQUENCE CHARACTERISTICS:
          (A) LENGTH:  38 base pairs
          (B) TYPE:  nucleic acid
          (C) STRANDEDNESS:  single-stranded
          (D) TOPOLOGY:  linear

    (ii) MOLECULE TYPE:
          (A) DESCRIPTION:  other nucleic acid

   (iii) HYPOTHETICAL:  no

    (iv) ANTI-SENSE:  no

    (xi) SEQUENCE DESCRIPTION:SEQ ID NO:   1:

ACCTGCACTA ACAGAAAAAA ACTAACAGAG ATGCAGGT                              38

(2) INFORMATION FOR SEQ ID NO:2:

     (i) SEQUENCE CHARACTERISTICS:
          (A) LENGTH:  23 base pairs
          (B) TYPE:  nucleic acid
          (C) STRANDEDNESS:  single-stranded
          (D) TOPOLOGY:  linear

    (ii) MOLECULE TYPE:
          (A) DESCRIPTION:  other nucleic acid

   (iii) HYPOTHETICAL:  no

    (iv) ANTI-SENSE:  no

    (xi) SEQUENCE DESCRIPTION:SEQ ID NO:   2:

GAAACTTTAA CAGTAATGCA GGT                                              23

(2) INFORMATION FOR SEQ ID NO:3:

     (i) SEQUENCE CHARACTERISTICS:
          (A) LENGTH:  22 base pairs
          (B) TYPE:  nucleic acid
          (C) STRANDEDNESS:  single-stranded
```

-continued (D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 3:

ACCTGCACTA ACAGCAATCA TG 22

(2) INFORMATION FOR SEQ ID NO:4:

(i) SEQUENCE CHARACTERISTICS:
(A) LENGTH: 14 base pairs
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 4:

NNNNNNNNGC AGGT 14

(2) INFORMATION FOR SEQ ID NO:5:

(i) SEQUENCE CHARACTERISTICS:
(A) LENGTH: 11 base pairs
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 5:

NNNNNGAGAC C 11

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 6:

GGGAAGCTTA CCTGCACTAA CAGNNATNNN 30

(2) INFORMATION FOR SEQ ID NO:7:

(i) SEQUENCE CHARACTERISTICS:
(A) LENGTH: 25 base pairs
(B) TYPE: nucleic acid

-continued (C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 7:

TATGAAAAAA ACTAACAGNN ATNNN 25

(2) INFORMATION FOR SEQ ID NO:8:

(i) SEQUENCE CHARACTERISTICS:
(A) LENGTH: 34 base pairs
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 8:

CTTTTTTTGA TTGTCNNTAC GTCCAGGGCC CACG 34

(2) INFORMATION FOR SEQ ID NO:9:

(i) SEQUENCE CHARACTERISTICS:
(A) LENGTH: 34 base pairs
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 9:

GCACCCGGGA CCTGCATATC TGTTACTTTT TTTC 34

(2) INFORMATION FOR SEQ ID NO:10:

(i) SEQUENCE CHARACTERISTICS:
(A) LENGTH: 34 base pairs
(B) TYPE: nucleic acid
(C) STRANDEDNESS: single-stranded
(D) TOPOLOGY: linear (ii) MOLECULE TYPE:
(A) DESCRIPTION: other nucleic acid (iii) HYPOTHETICAL: no (iv) ANTI-SENSE: no (xi) SEQUENCE DESCRIPTION:SEQ ID NO: 10:

GCACCCGGGA CCTGCATCTC TGTTAGTTTT TTTC 34

(2) INFORMATION FOR SEQ ID NO:11:

(i) SEQUENCE CHARACTERISTICS:
(A) LENGTH: 34 base pairs

-continued

```
        (B) TYPE:  nucleic acid
        (C) STRANDEDNESS:  single-stranded
        (D) TOPOLOGY:  linear

   (ii) MOLECULE TYPE:
        (A) DESCRIPTION:  other nucleic acid

  (iii) HYPOTHETICAL:  no

   (iv) ANTI-SENSE:  no

   (xi) SEQUENCE DESCRIPTION:SEQ ID NO:   11:

GCACCCGGGA CCTGCATTGC TGTTAGTTTT TTTC                             34


(2) INFORMATION FOR SEQ ID NO:12:

    (i) SEQUENCE CHARACTERISTICS:
        (A) LENGTH:  34 base pairs
        (B) TYPE:  nucleic acid
        (C) STRANDEDNESS:  single-stranded
        (D) TOPOLOGY:  linear

   (ii) MOLECULE TYPE:
        (A) DESCRIPTION:  other nucleic acid

  (iii) HYPOTHETICAL:  no

   (iv) ANTI-SENSE:  no

   (xi) SEQUENCE DESCRIPTION:SEQ ID NO:   12:

GCACCCGGGA CCTGCATATC TGTTAGTTTT TTTC                             34
```